United States Patent
Rehwald et al.

(10) Patent No.: US 8,086,297 B2
(45) Date of Patent: Dec. 27, 2011

(54) DARK BLOOD DELAYED ENHANCEMENT MAGNETIC RESONANCE VIABILITY IMAGING TECHNIQUES FOR ASSESSING SUBENDOCARDIAL INFARCTS

(75) Inventors: Wolfgang Rehwald, Chapel Hill, NC (US); Michael Salerno, Durham, NC (US)

(73) Assignee: Duke University, Durham, NC (US)

( * ) Notice: Subject to any disclaimer, the term of this patent is extended or adjusted under 35 U.S.C. 154(b) by 951 days.

(21) Appl. No.: 11/957,520

(22) Filed: Dec. 17, 2007

(65) Prior Publication Data
US 2009/0005673 A1    Jan. 1, 2009

Related U.S. Application Data

(60) Provisional application No. 60/887,596, filed on Jan. 31, 2007.

(51) Int. Cl.
*A61B 5/05* (2006.01)

(52) U.S. Cl. ........ 600/420; 600/407; 600/410; 600/413; 600/419

(58) Field of Classification Search .................. 600/407, 600/410, 419, 420
See application file for complete search history.

(56) References Cited

U.S. PATENT DOCUMENTS

| | | | |
|---|---|---|---|
| 5,297,550 | A | 3/1994 | Margosian |
| 5,422,576 | A | 6/1995 | Kao et al. |
| 6,205,349 | B1 | 3/2001 | Kim et al. |
| 6,340,887 | B1 | 1/2002 | Liu et al. |
| 6,397,096 | B1 | 5/2002 | Liu et al. |
| 6,498,946 | B1 | 12/2002 | Foo et al. |
| 6,526,307 | B2 | 2/2003 | Foo |
| 7,020,314 | B1 | 3/2006 | Suri et al. |
| 7,315,756 | B2 | 1/2008 | Yarnykh et al. |
| 2002/0087067 | A1* | 7/2002 | Foo ................................ 600/413 |
| 2003/0069493 | A1 | 4/2003 | Pan et al. |
| 2004/0049106 | A1 | 3/2004 | Kanazawa |
| 2004/0133098 | A1 | 7/2004 | Yarnykh et al. |
| 2005/0245809 | A1* | 11/2005 | Wolff et al. .................... 600/410 |
| 2006/0007429 | A1 | 1/2006 | Emer et al. |
| 2006/0074291 | A1 | 4/2006 | Hardy et al. |
| 2006/0099148 | A1 | 5/2006 | Fisher et al. |
| 2007/0038069 | A1* | 2/2007 | Itagaki et al. ................. 600/410 |
| 2007/0243136 | A1 | 10/2007 | Fisher et al. |

OTHER PUBLICATIONS

McGill University, "Wiggers Diagram," Jan. 3, 2000. pp. 1-2.*
Foo, Thomas K., et al., "Enhanced Viability Imaginig: Improved Contrast in Myocardial Delayed Enhancement Using Dual Inversion Time Subtraction," Magnetic Resonance in Medicine 53:1484-1489 (2005).
Sievers, Burkhard, et al., "Rapid Detection of Myocardial Infarction by Subsecond, Free-Breathing Delayed Contrast-Enhancement Cardiovascular Magnetic Resonance," Circulation Journal of the American Heart Association (2007).

(Continued)

*Primary Examiner* — James Kish
(74) *Attorney, Agent, or Firm* — Nixon & Vanderhye PC

(57) ABSTRACT

The technology herein provides a dark blood delayed enhancement technique that improves the visualization of subendocardial infarcts that may otherwise be disguised by the bright blood pool. The timed combination of a slice-selective and a non-selective preparation improves the infarct/blood contrast by decoupling their relaxation curves thereby nulling both the blood and the non-infarcted myocardium. This causes the infarct to be imaged bright and the blood and non-infarct to both be imaged dark. The slice-selective preparation occurs early enough in the cardiac cycle so that fresh blood can enter the imaged slice.

15 Claims, 22 Drawing Sheets

OTHER PUBLICATIONS

Schad, Lothar R., et al., "Magnetic Resonance Urography Using a Saturation Inversion Projection Spinecho Sequence," Magn Reson Imaging, p. 889, ncbi.nlm.nih.gov (1993).

Oesingmann, Niels, et al., "Optimization of a Saturation Inversion Projektion (SIP) Spin Echo (SE) Sequence for Magnetic Resonance Urography," Proceedings of the Society of Magnetic Resonance, vol. 1993, Issue S3, p. 1227.

Redpath, T.W., et al, A Double Inversion Recovery Sequence for Simultaneous Suppression of Lipid and Fluid Signals, p. 1194 (1987).

Gui, Dawei, et al., "Fast Magnetization-Driven Preparation for Imaging of Contrast-Enhanced Coronary Arteries During Intra-Arterial Injection of Contrast Agent," Journal of Magnetic Resonance Imaging 24:1151-1158 (2006).

Song, Hee Kwon, et al., "Multislice double inversion pulse sequence for efficient black-blood MRI," Magnetic Resonance in Medicine, vol. 47, issue 3, pp. 616-620 (Feb. 20, 2002).

Desai, Milind Y., et al., "Delayed Contrast-Enhanced MRI of the Aortic Wall in Takayasu's Arteritis: Initial Experience," American Journal of Roentgenology, 184: 1427-1431 (2005).

Berr, Stuart S., et al., "Black blood gradient echo cine magnetic resonance imaging of the mouse heart," Magnetic Resonance in Medicine, vol. 53, Issue 5, pp. 1074-1079 (Apr. 20, 2005).

Campos, S., et al., "New black blood pulse sequence for studies of the heart," The International Journal of Cardiac Imaging, vol. 15, No. 2 (Apr. 1999).

Klepac, Steven R., et al., "Cardiac MRI—Technical Aspects Primer," emedicine from WebMD, (Jul. 2005).

Albert, Timothy S.E., "Determining Myocardial Viability with MR Imaging," 38th Annual New York City Cardiovascular Symposium (Dec. 11, 2005).

Rehwald, Wolfgang G., et al., "Myocardial Magnetic Resonance Imaging Contrast Agent Concentrations After Reversible and Irreversible Ischemic Injury," Circulation, Journal of the American Heart Association, pp. 224-229 (2002).

Kim, Raymond J., et al., "Relationship of MRI Delayed Contrast Enhancement to Irreversible Injury, Infarct Age, and Contractile Function," Circulation, Journal of the American Heart Association, pp. 1992-2992 (1999).

Simonetti, Orlando, et al., "2D and 3D Segmented TurboFLASH for the Visualization of Myocardial Injury," Proc. Intl. Soc. Mag. Reson. Med 8 (2000).

Simonetti, Orlando, et al., "An Improved MR Imaging Technique for the Visualization of Myocardial Infarction," Radiology 2001, vol. 218, No. 1, pp. 215-223 (2001).

Edelman RR, et al. "Fast selective black blood MR imaging," Radiology, 1991;181(3):655-660.

Simonetti OP,et al, "Black blood T2-weighted inversion-recovery MR imaging of the heart," Radiology. 1996;199 (1):49-57.

Yarnykh VL, et al, "T1-insensitive flow suppression using quadruple inversion recovery," Magn Reson Med. 2002;48(5):899-905.

Rehwald WG, et al, "Dark blood delayed enhancement in humans by double preparation and gradient-echo or turbo-spin-echo readout," Proc Intl Soc Magn Reson Med. 2007.

Salerno et al, "Contrast optimization of blackblood viability imaging," Proc Intl Soc Magn Reson Med. 2007.

Ibrahim EL SH, et al, "Stimulated-echo acquisition mode (STEAM) MRI for black-blood delayed hyperenhanced myocardial imaging," J Magn Reson Imaging. 2008;27(1):229-238.

Kellman P, et al, "Multi-contrast delayed enhancement provides improved contrast between myocardial infarction and blood pool," J Magn Reson Imaging. 2005;22(5):605-613.

Liu CY, et al, "Improved delayed enhanced myocardial imaging with T2-Prep inversion recovery magnetization preparation," J Magn Reson Imaging. 2008;28(5):1280-1286.

Borrello JA et al, "Regional phase correction of inversion-recovery MR images," Magn Reson Med. 1990;14 (1):56-67.

Xiang QS, "Inversion recovery image reconstruction with multiseed region-growing spin reversal," J Magn Reson Imaging. 1996;6(5):775-782.

* cited by examiner

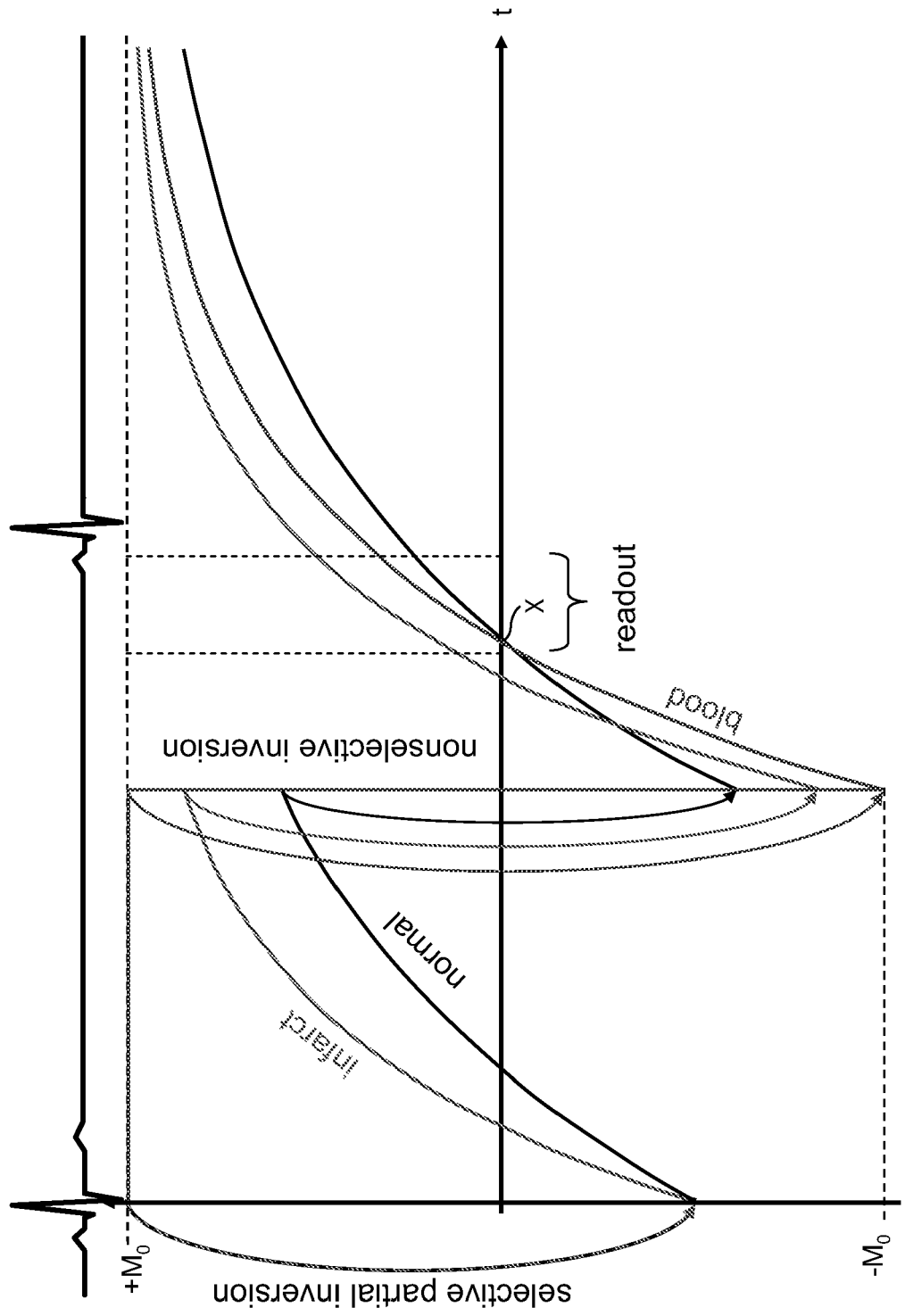

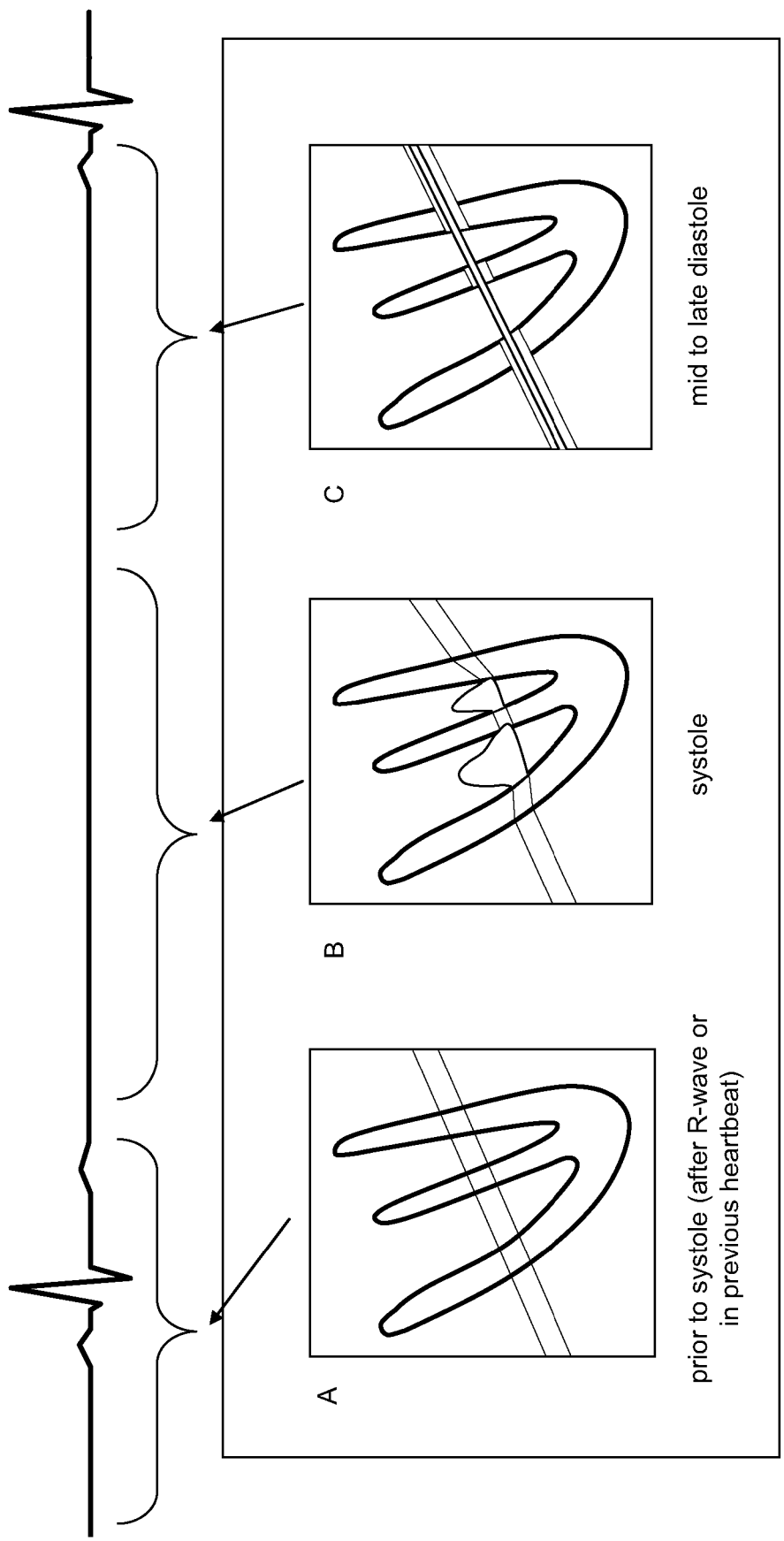
FIG. 2D: Exemplary Slice-Selective Preparation and Blood-Exchange

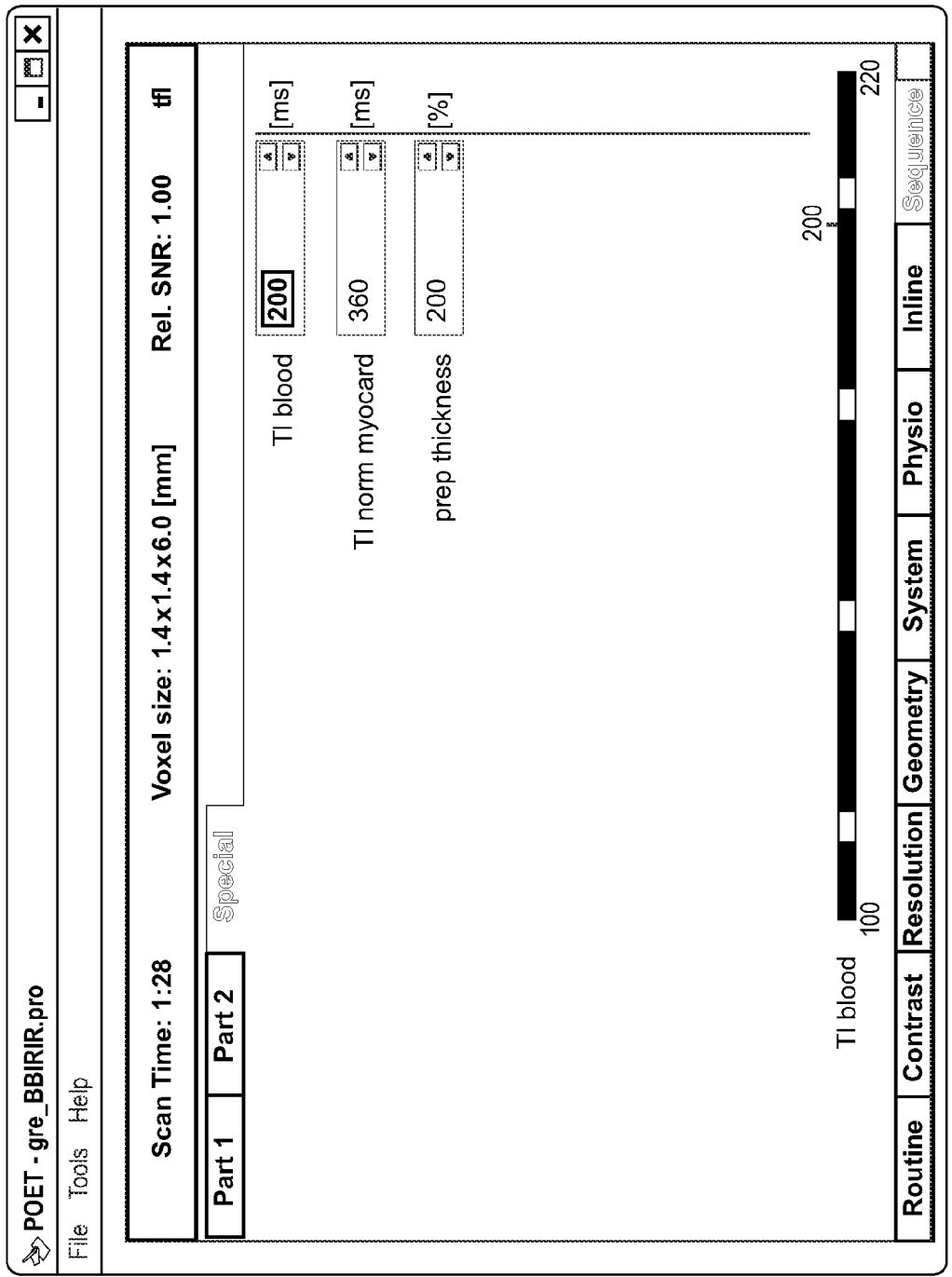
FIG. 2E : Example User Interface

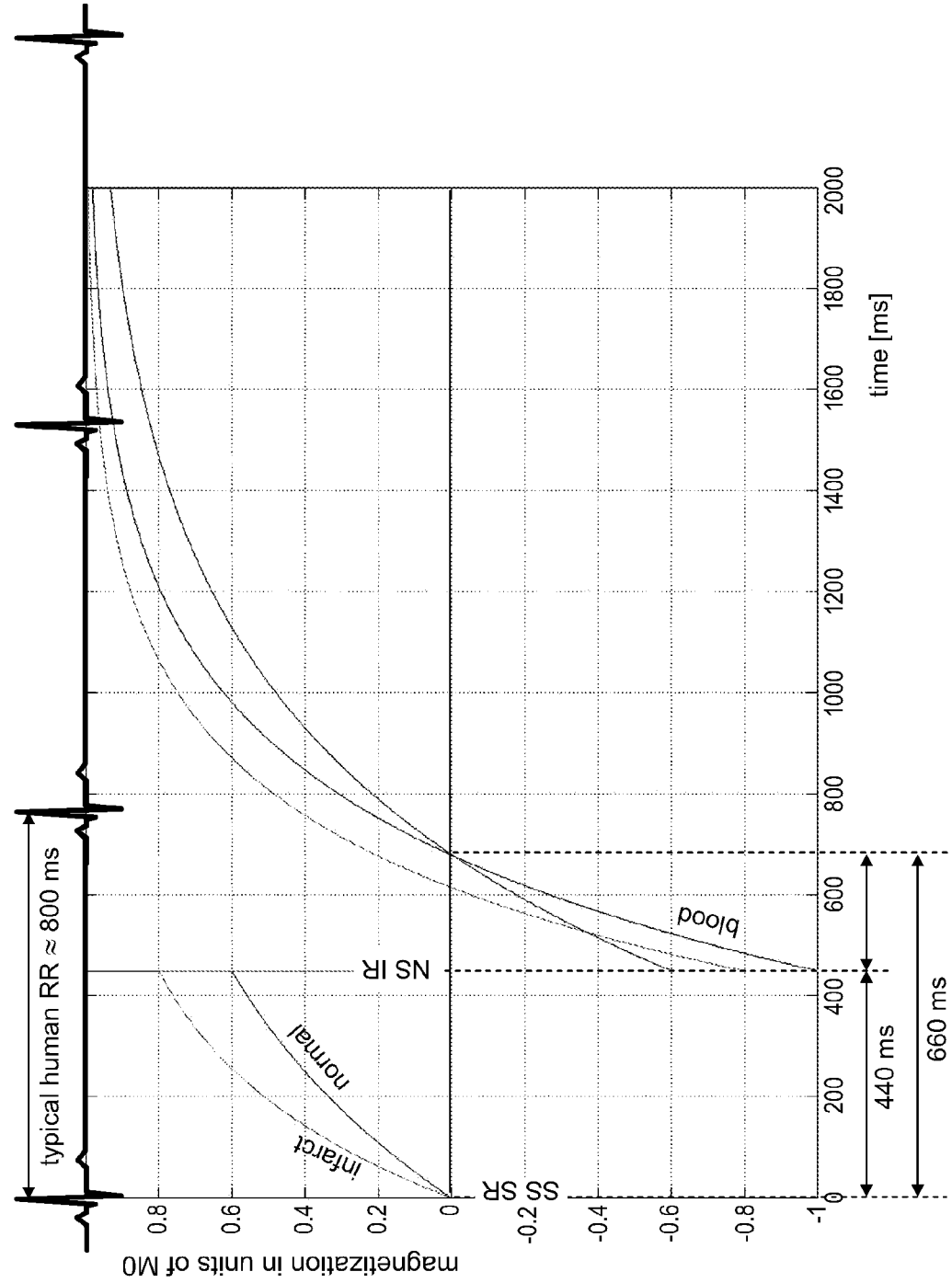

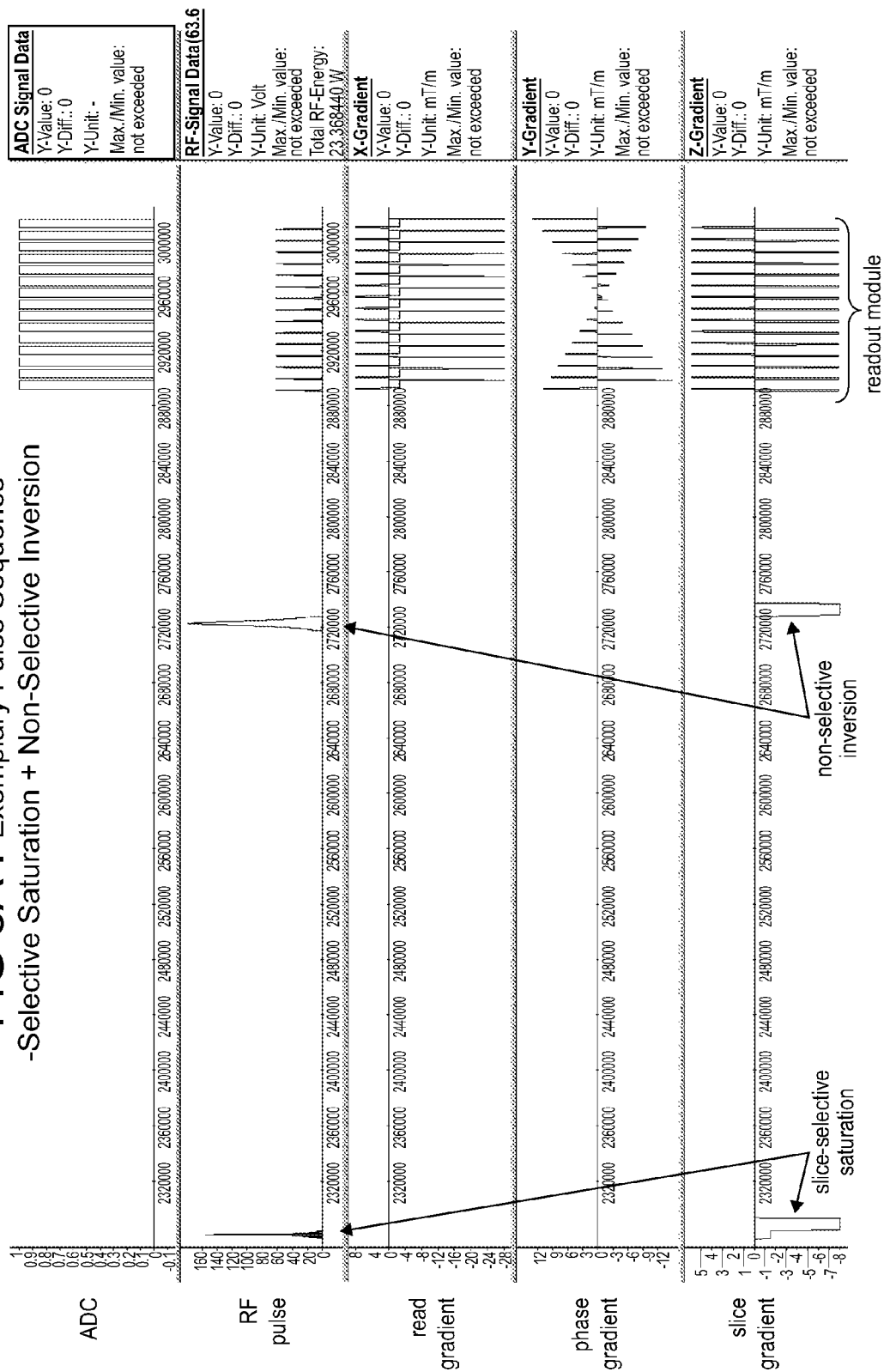

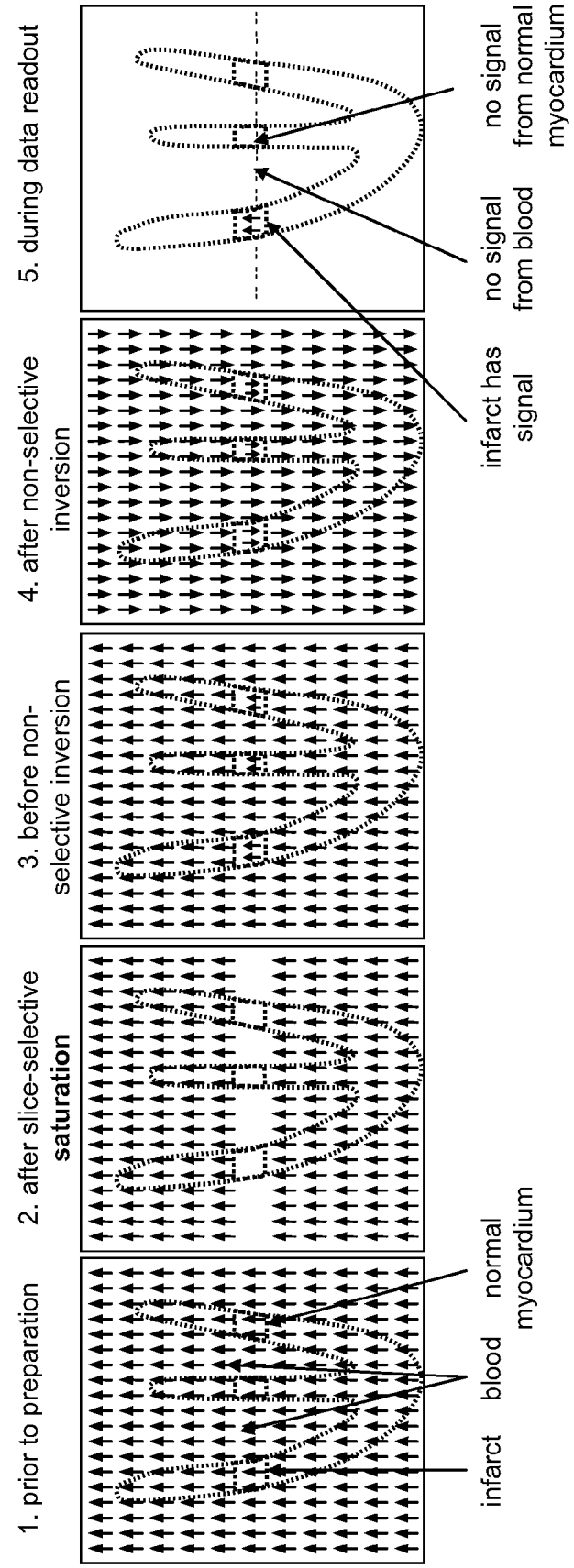
FIG. 3B: Exemplary slice-selective saturation magnetization

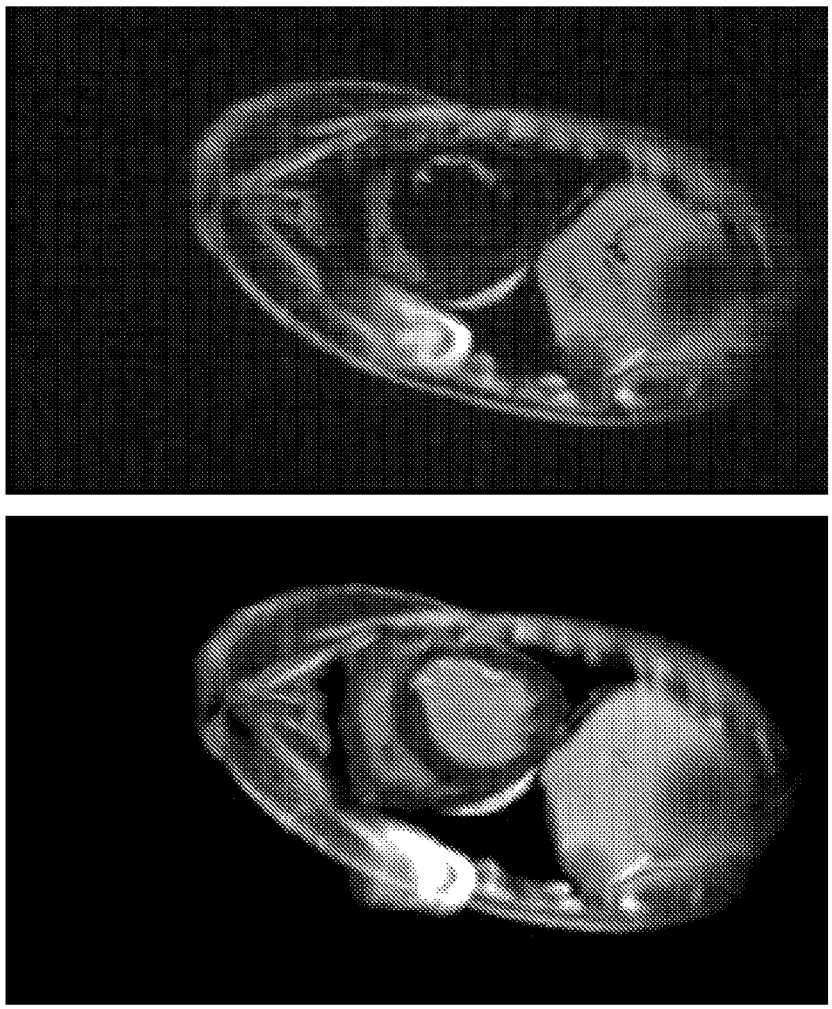

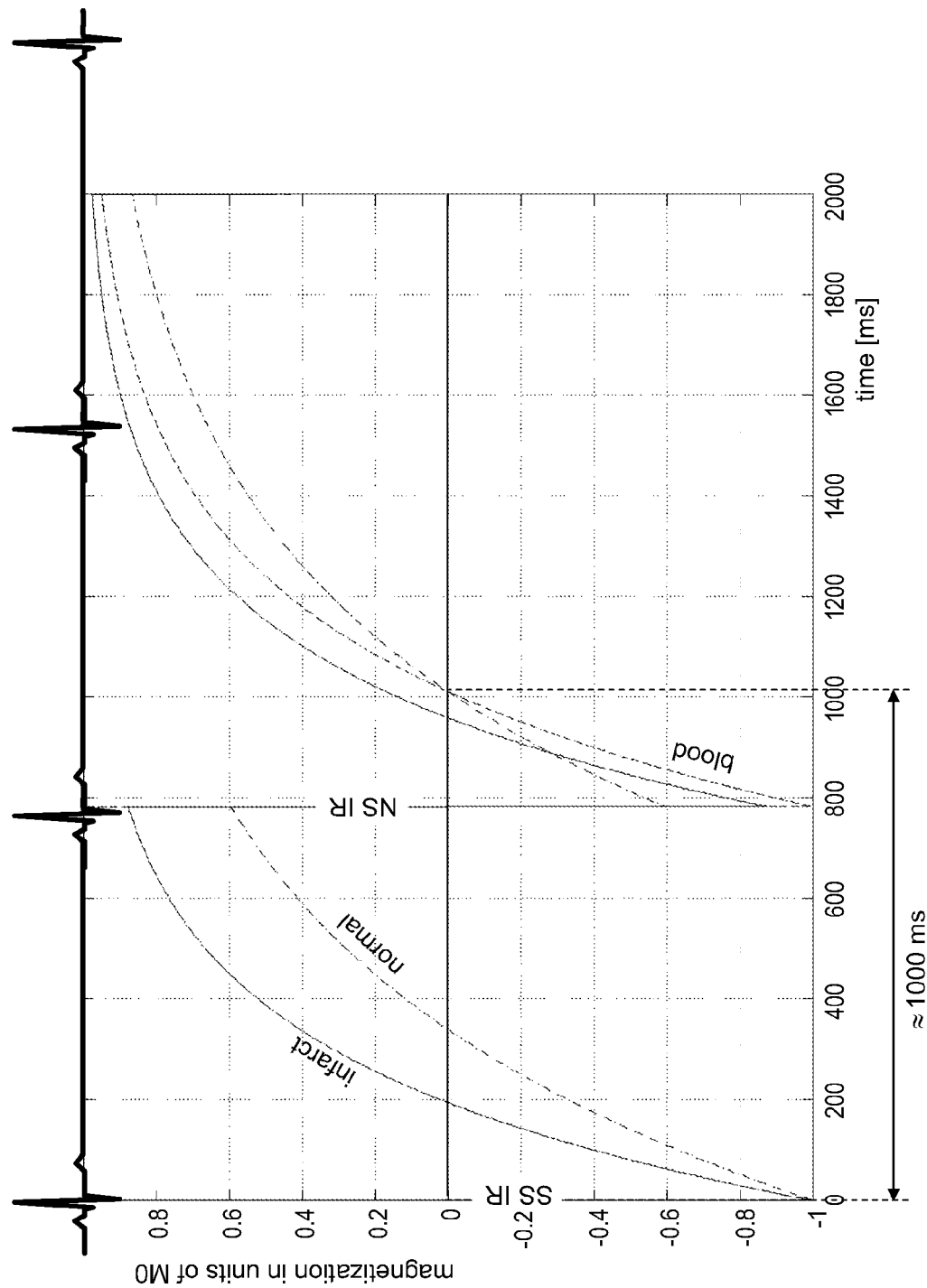

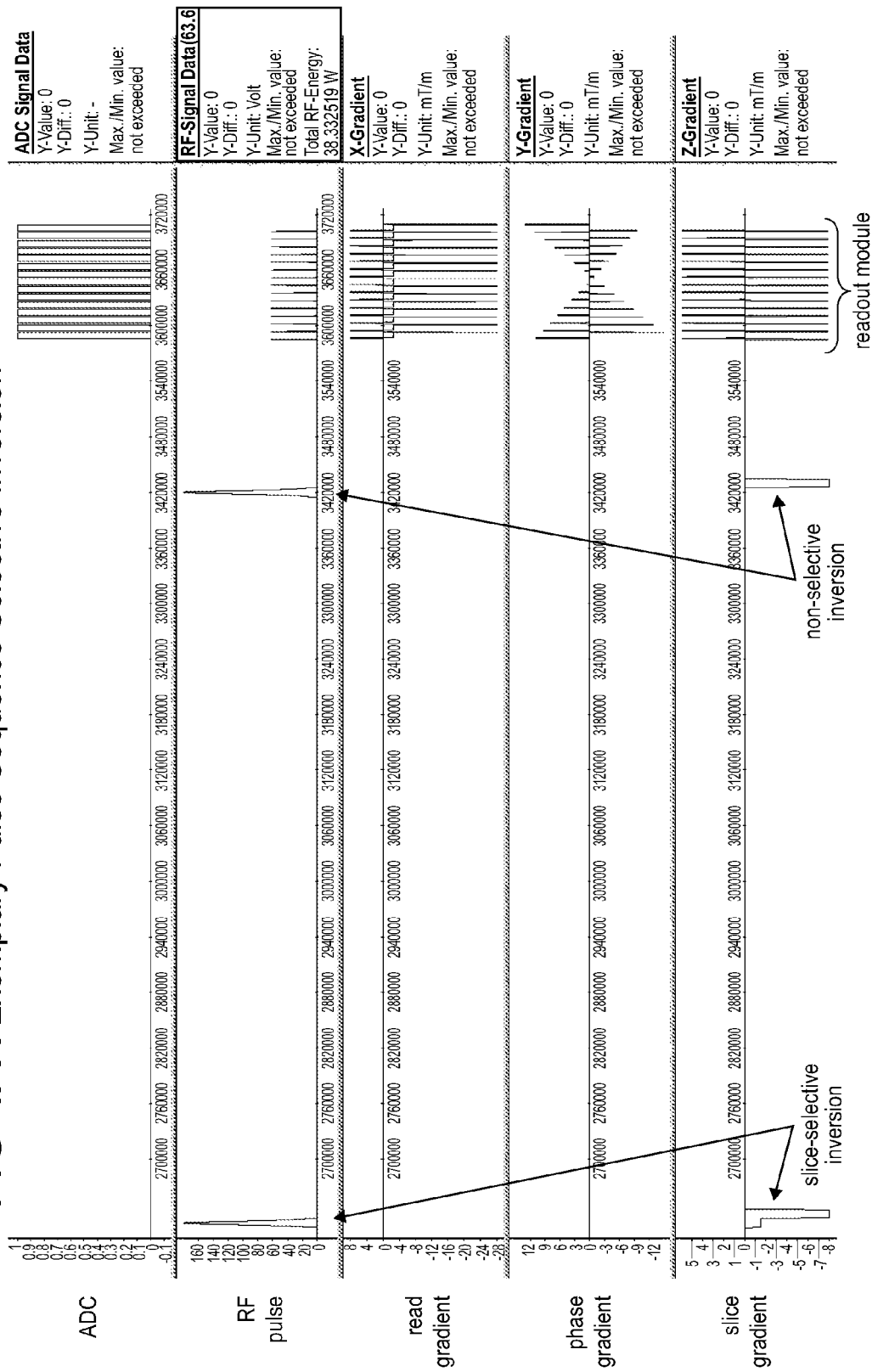

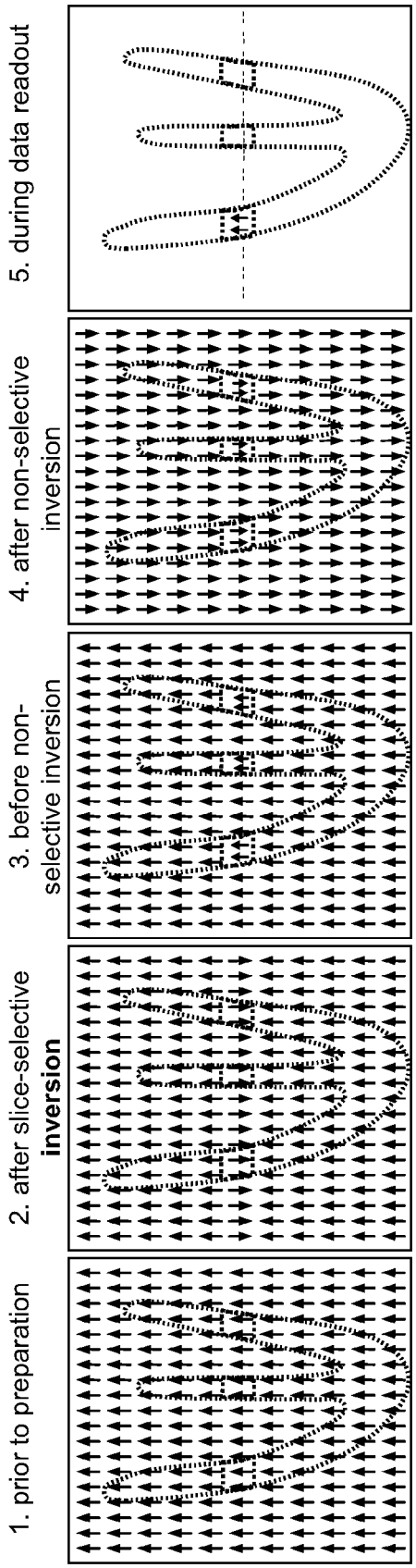

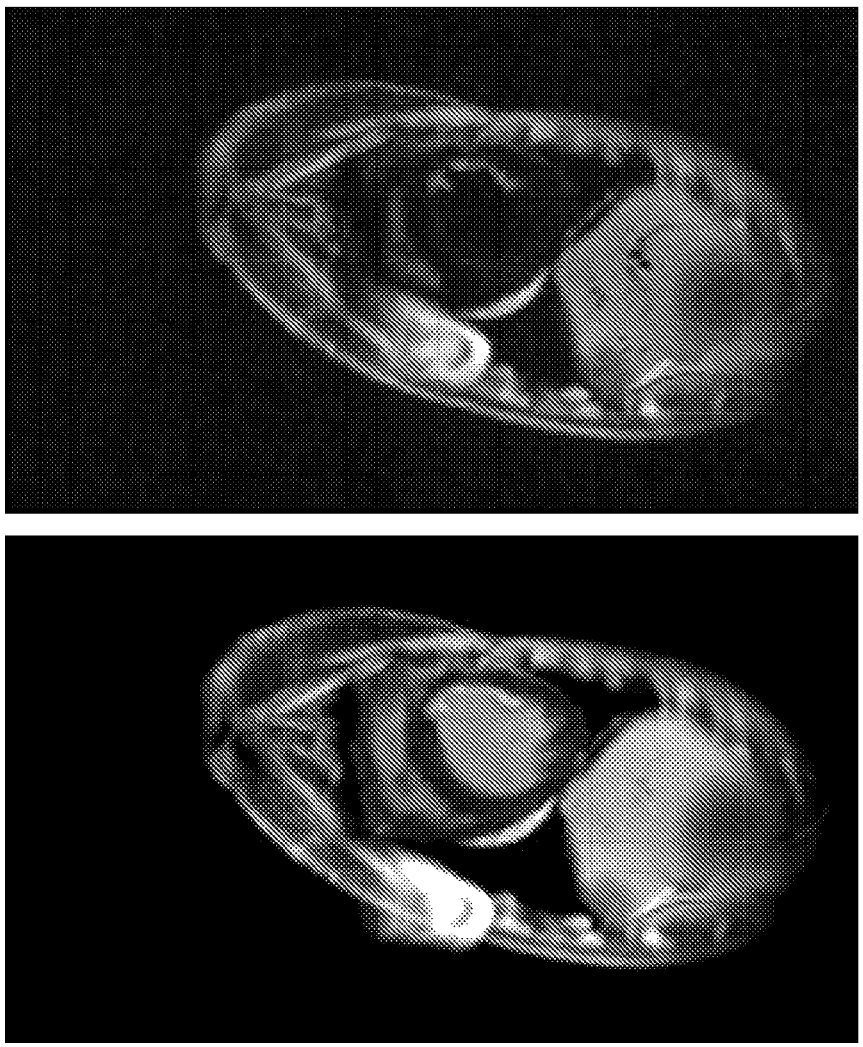

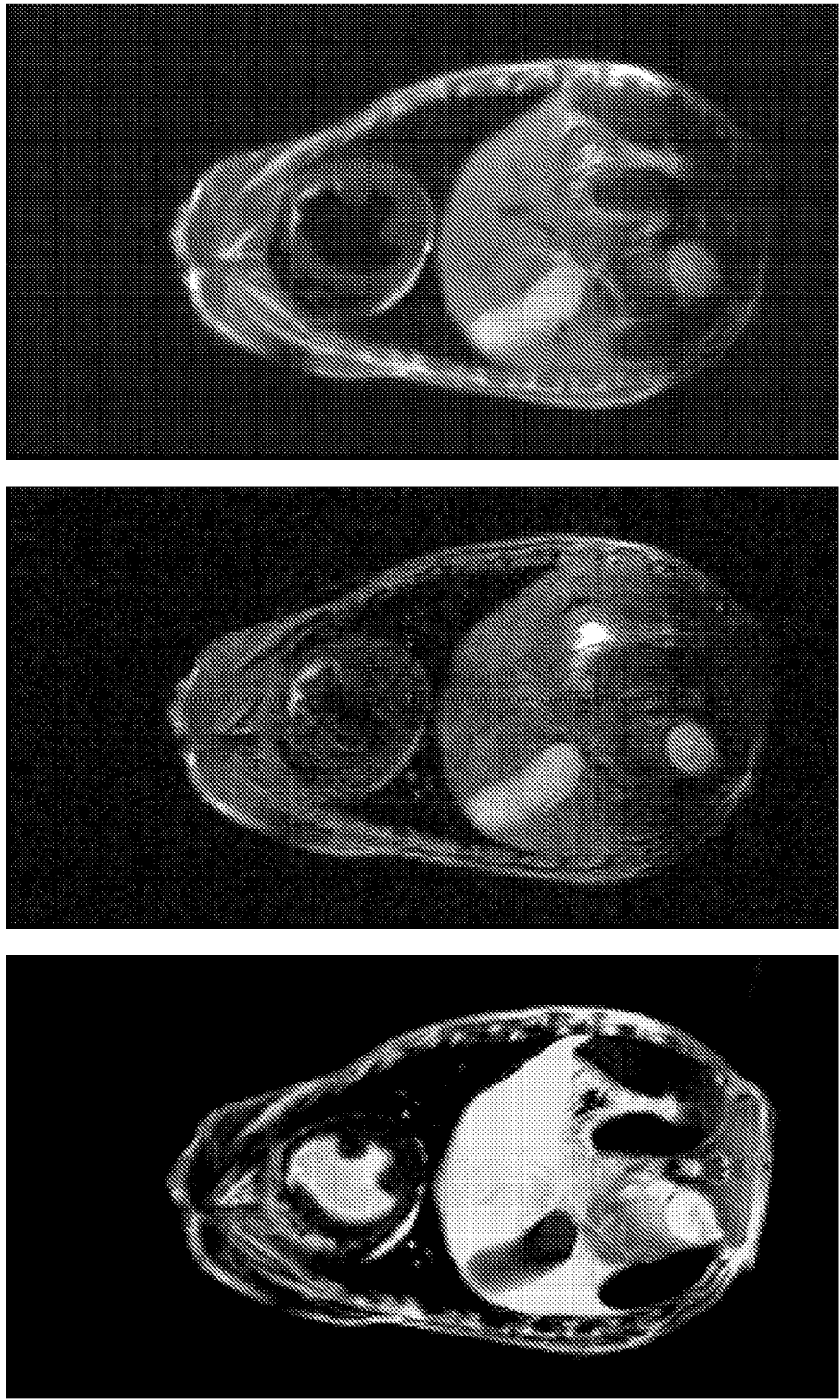

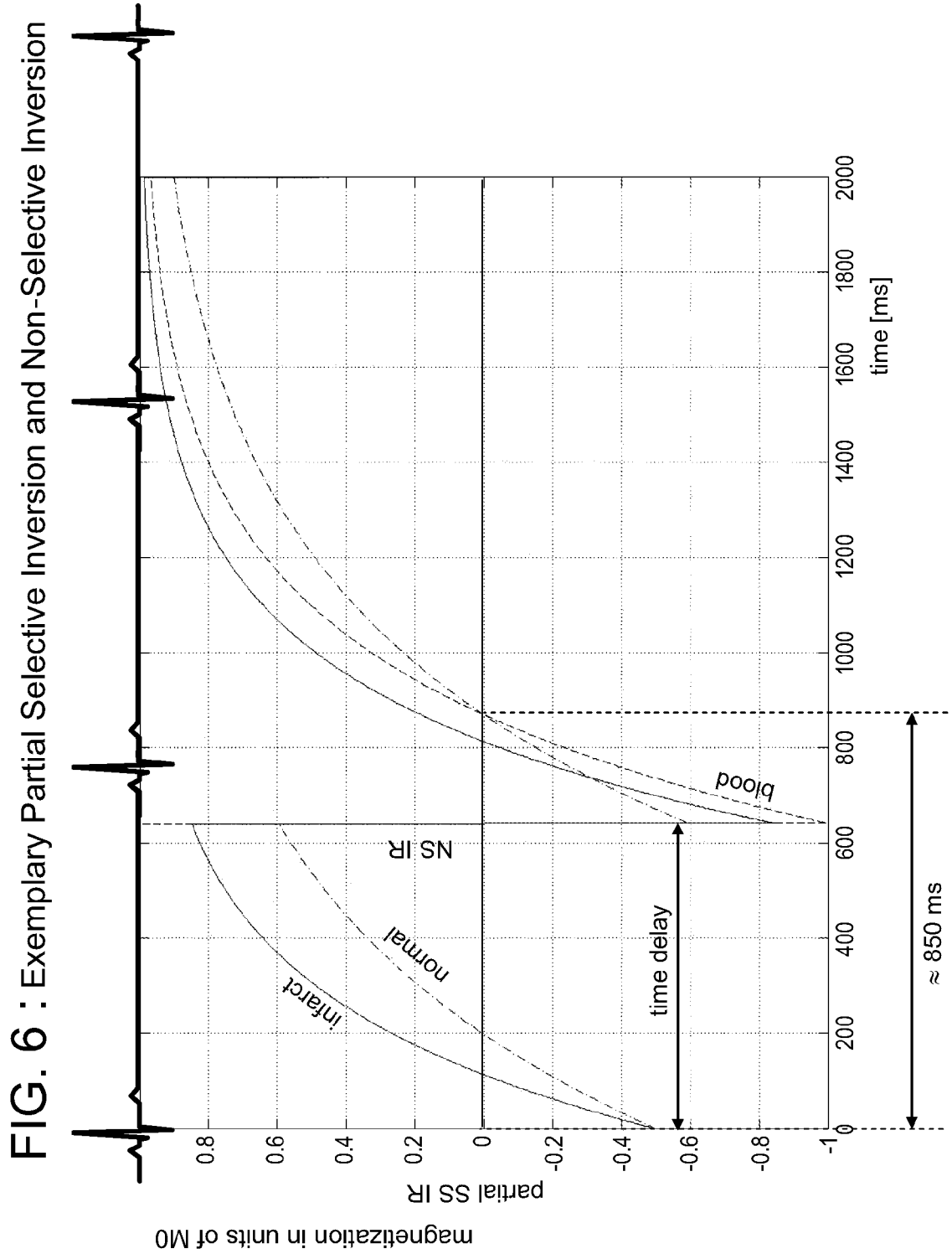
FIG. 6: Exemplary Partial Selective Inversion and Non-Selective Inversion

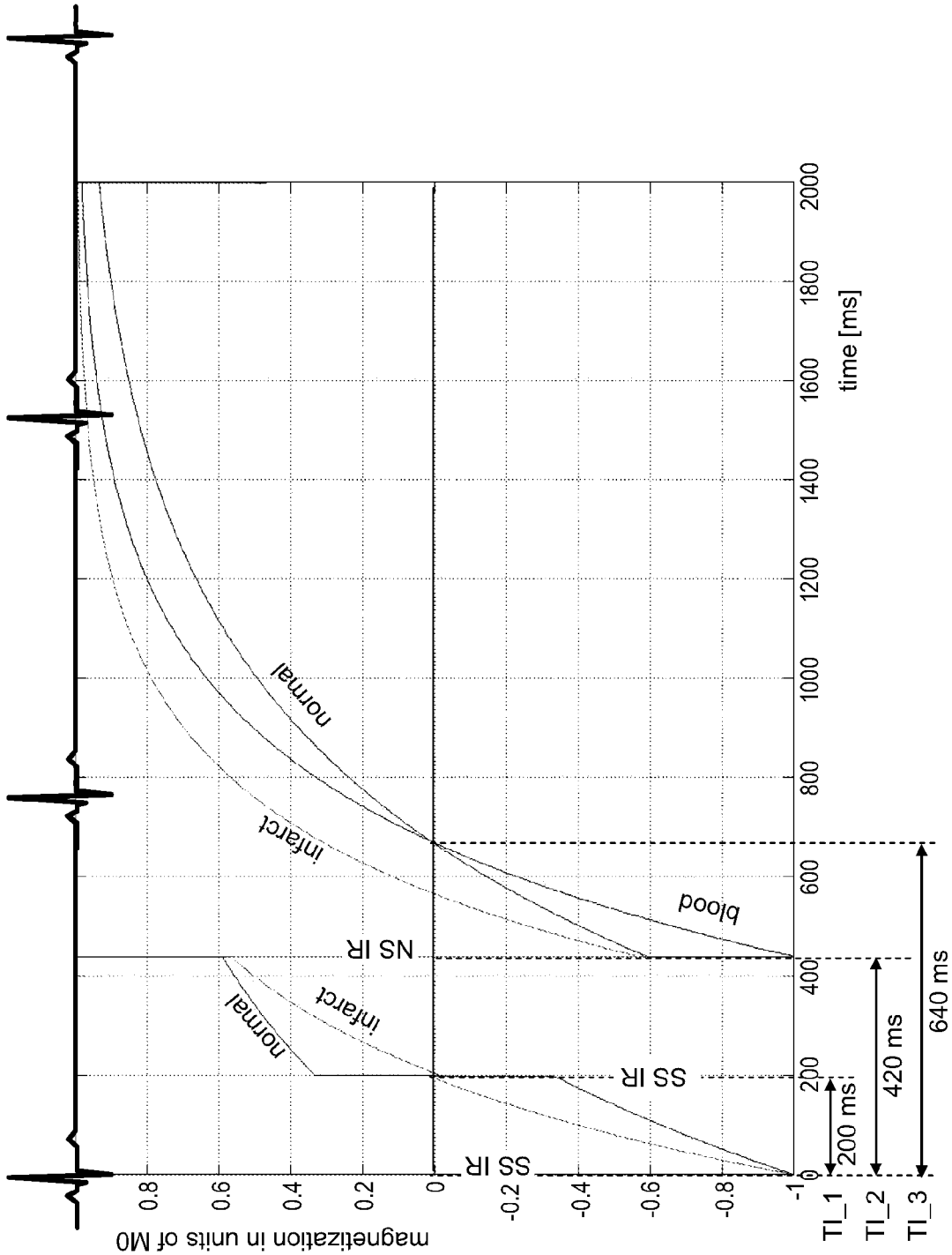
FIG. 7 : Two Selective Inversions and a Non-Selective Inversion

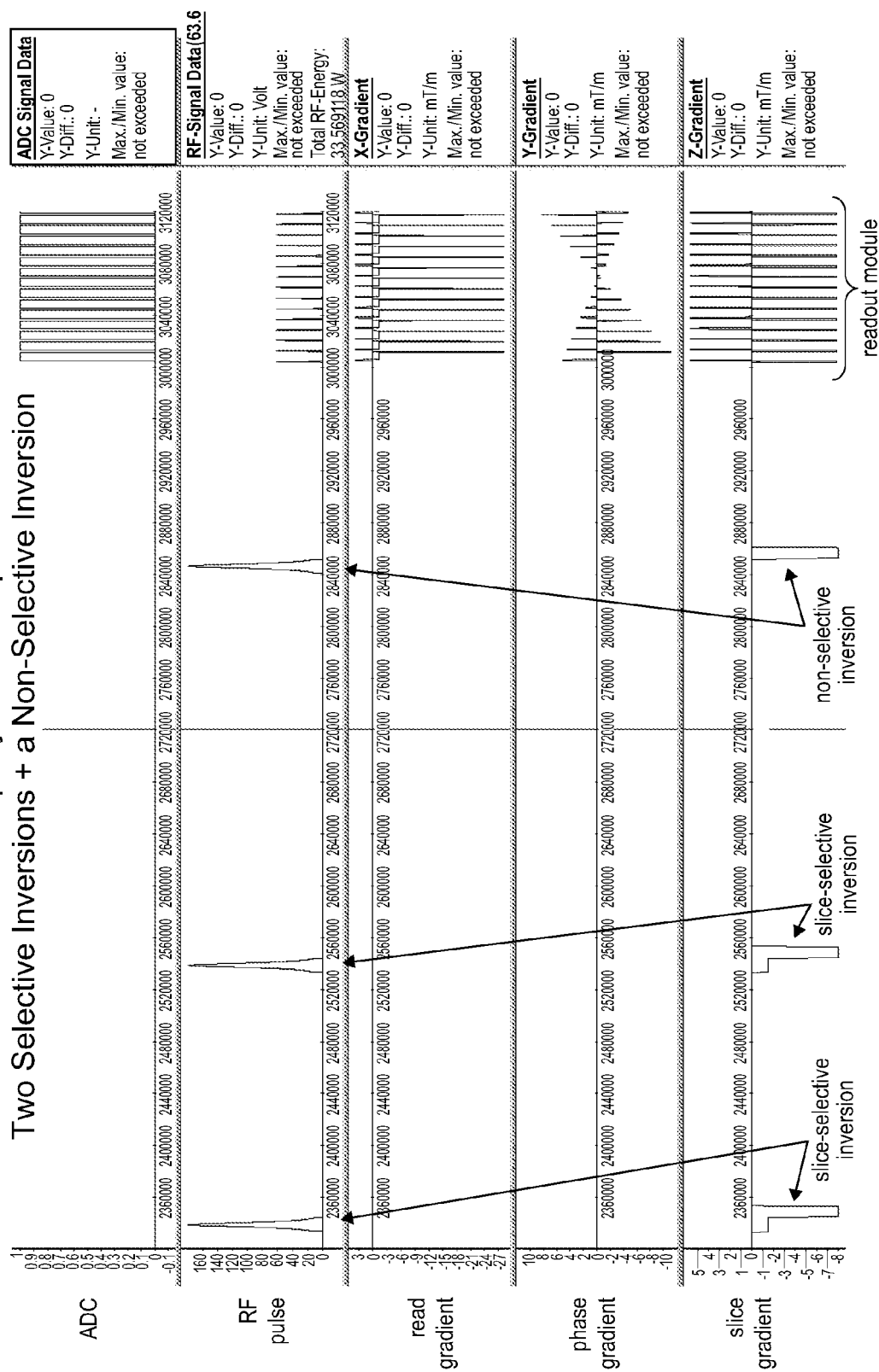

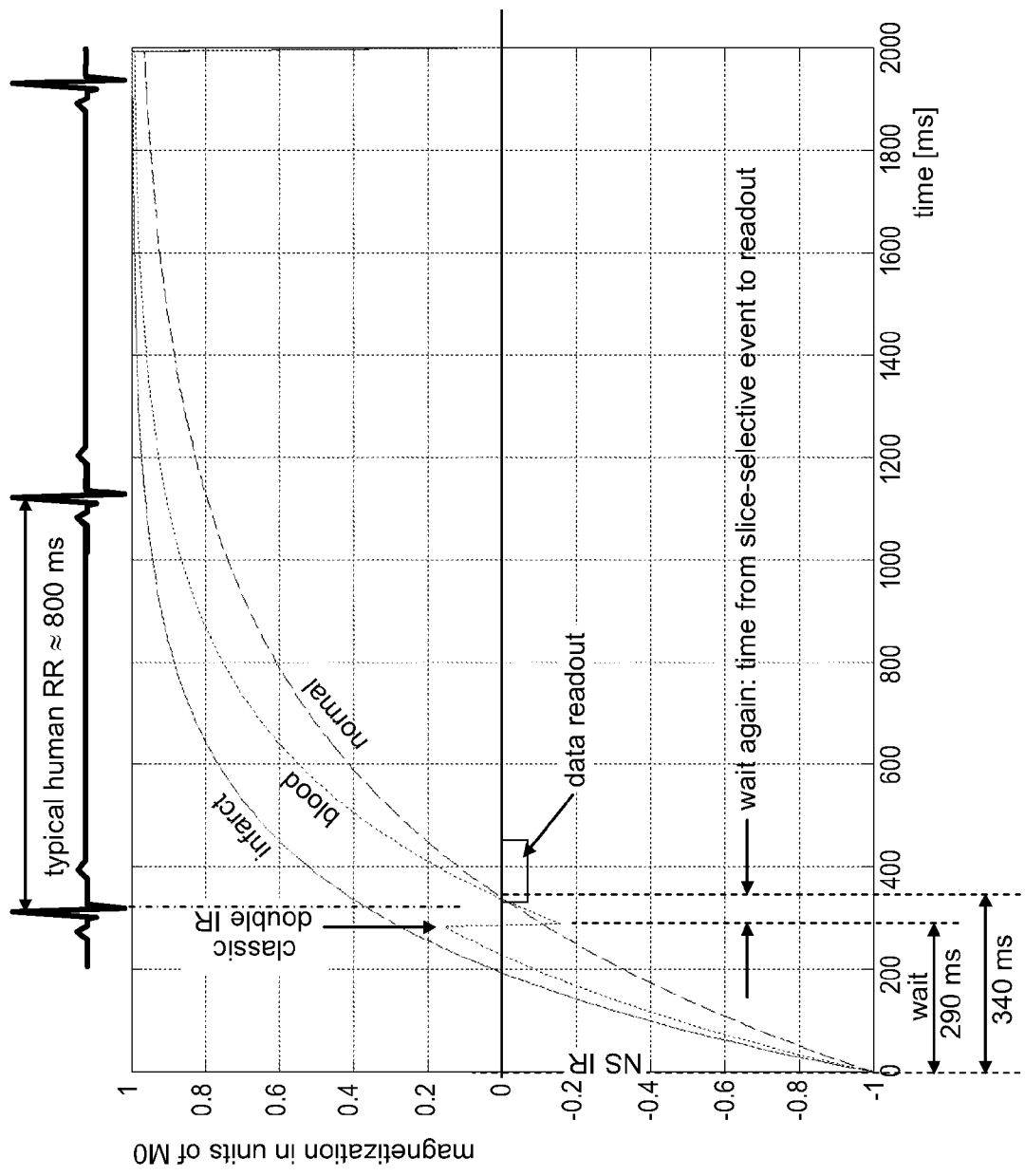
FIG. 9: Exemplary Non-Selective IR Followed by timed Classic Double IR

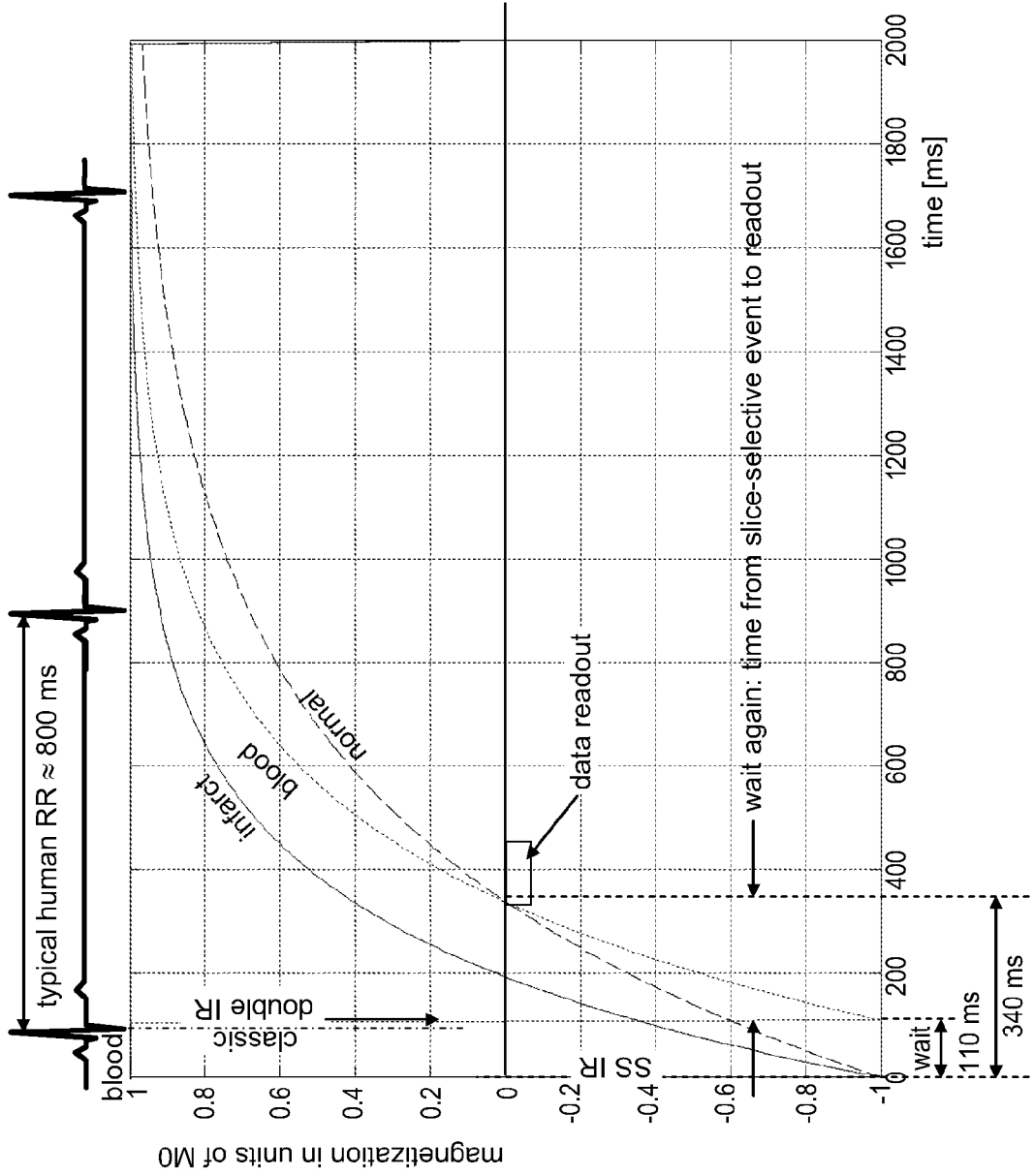
FIG. 10: Exemplary Slice-Selective IR Followed by timed Classic Double IR Exemplary Dog Cardiac Images
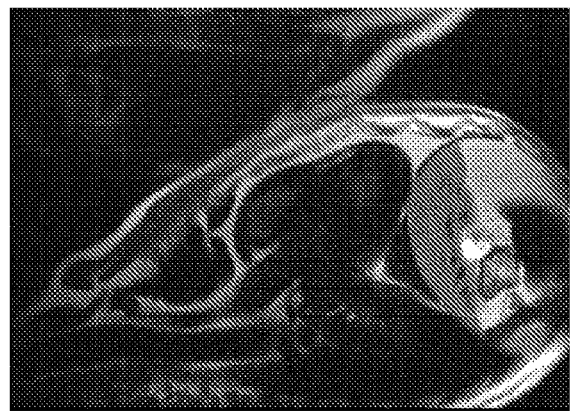
FIG. 12B
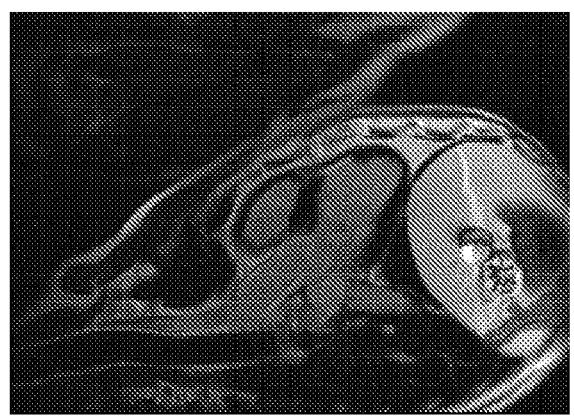
FIG. 12A
FIG. 11A
FIG. 11B

Exemplary Dog Cardiac Images

Exemplary Human Cardiac Images

DARK BLOOD DELAYED ENHANCEMENT MAGNETIC RESONANCE VIABILITY IMAGING TECHNIQUES FOR ASSESSING SUBENDOCARDIAL INFARCTS

CROSS-REFERENCES TO RELATED APPLICATIONS

This application claims the benefit of priority from provisional application No. 60/887,596 filed Jan. 31, 2007, incorporated herein by reference

TECHNOLOGICAL FIELD

The technology herein relates to magnetic resonance imaging (MRI) pulse sequences for use in detecting infarct (dead heart cells or scars) in the human heart, and more particularly to black blood viability magnetic resonance imaging (MRI) techniques that render blood and non-infarcted myocardium dark and infarct bright.

BACKGROUND AND SUMMARY

Myocardial infarction (MI) occurs in almost a million people each year in the United States, where coronary heart disease is the leading cause of hospital admissions. According to the joint American College of Cardiology and European Society of Cardiology consensus document concerning the redefinition of MI, the diagnosis of MI is often based on cardiac biomarkers and ECG changes. However, biomarkers are only elevated for 4 to 10 days after an acute event. Thus, biomarkers are not useful for the diagnosis of subacute or chronic MI. The ECG also has limitations: Q waves that form the fundamental basis of the diagnosis of chronic MI may be absent or, if initially present, may disappear at a later time point.

Cardiovascular magnetic resonance (CMR) imaging is a highly attractive modality for the assessment of myocardial infarction and viability because of high spatial resolution and accuracy. However, practical drawbacks have in the past limited the impact of such technology for general clinical use. For example, standard CMR is generally more complex as compared to some imaging modalities. Patient and protocol setup times have been generally longer, and multiple breath-holds and longer scanning times have been necessary. These conditions can limit clinical throughput and the types of patients that can be scanned, and may also increase the complexity and length of CMR training.

In view of the importance of this area of investigation to societal health, much work has been done in the past to develop imaging techniques capable of detecting infarcts and determining viability.

For example, work at Northwestern University by Dr. Raymond J. Kim and others resulted in U.S. Pat. No. 6,205,349 entitled "Differentiating normal living myocardial tissue, injured living myocardial tissue, and infarcted myocardial tissue in vivo using magnetic resonance imaging", describing techniques for distinguishing between normal, injured but living, and infarcted myocardium using MR imaging. Because they solve many of the challenges described above, such delayed contrast-enhancement CMR techniques have become the gold standard for imaging myocardial infarction. Such delayed enhancement images exhibit excellent contrast between normal and infracted myocardium due to nulling of normal myocardium. The current clinical standard is a so-called segmented IR-Turbo Flash technology that acquires data during a breath hold of typically 10 seconds or less. Furthermore, using such delayed contrast enhancement techniques, myocardial infarction can be detected rapidly by sub-second delayed contrast-enhancement CMR during free breathing with high accuracy. The clinical implication is that delayed contrast-enhancement CMR can approach a quick "push-button" technique with the ability to scan a wide range of patients, including those who are more acutely ill, those with dyspnea, or those unable to undergo a prolonged examination. Moreover, clinical throughput could be increased multifold. See e.g., Sievers et al, "Rapid Detection of Myocardial Infarction by Subsecond, Free-Breathing Delayed Contrast-Enhancement Cardiovascular Magnetic Resonance", *Circulation* 2007;115;236-244 and other articles by Drs. Kim, Judd and/or Rehwald.

Such known prior art delayed enhancement MRI pulse sequences can deliver images in which viable myocardium (living heart tissue) appears dark and infarct and blood appears bright. For example, a frequently used exam in cardiovascular MRI is called "viability imaging" or "myocardial delayed enhancement." For this test, a MR contrast agent is injected into the patient intravenously while the patient is lying in the MRI scanner. After about 10 minutes, the contrast agent has distributed throughout the patient's body including the heart. In the heart, this agent accumulates primarily in dead heart cells and in scar, both known as infarcted territory (such cells have died e.g., due to a prior heart attack—infarct). As the contrast agent regionally alters the magnetic properties of the heart tissue and as it primarily accumulates in the dead cells, it is possible to visualize regions of dead cells with MRI.

One so-called "pulse sequence" provided by software running on a MRI scanner that can be used to provide such imaging is called Inversion Recovery Turbo Fast Low Angle Shot (IR–TurboFlash). This is the vendor acronym of Siemens Medical Solutions. Other vendors such as GE Medical Systems and Philips have similar products with different acronyms. Such methods reliably deliver images in which viable myocardium (living heart cells) appears dark, and infarct (dead heart cells or scar) and blood appear bright.

Such techniques as described above are sufficient in many cases to detect infarcts and help physicians determine myocardial viability. For example, the identification of large areas of dysfunctional but viable myocardium predicts situations where revascularization is likely to improve functional class, augment regional and global LVEF and increase survival. Conversely, the presence of predominant myocardial scarring predicts increased operative mortality and the absence of these salutary effects.

While such "bright blood" imaging and analysis techniques have been successful, it has become evident that in patients with small subendocardial infarcts (infarcts located at the inner side of the heart wall adjacent to the blood pool), the bright blood can sometimes obscure the bright infarct. Small subendocardial infarcts are sometimes difficult to detect as they may have a similar signal intensity (T1 values) as the blood pool. Therefore, small subendocardial infarcts are often hard to detect in standard delayed enhancement images. The infarct may be missed or its size may be underestimated. Ideally, a viability sequence would have excellent contrast between infarct and both normal myocardium and the blood pool. Techniques providing images in which blood appears dark/black while leaving the infarct bright and normal myocardium dark have been highly sought after.

So-called "dark blood" or "black blood" angiography MRI pulse sequences are known. Such techniques make flowing blood appear dark or black in the image and make stationary blood or tissue appear to be bright in the image. In one such type of "black blood" pulse sequence, early echoes are more heavily proton density weighted than later echoes (the later echoes can be more T2 weighted). Depending on the exact sequence implementation, the obtained images can be more proton-weighted or more T2-weighted.

Also, the idea of combining a slice-selective with a non-selective inversion pulse has been used for several years for acquiring black-blood images. However, generally the two pulses are played immediately after one another. A known technique called "Black-Blood HASTE" is usually used without the presence of contrast agent in the blood pool, and it only nulls (makes black) blood, not normal myocardium.

For example, it is generally known that nulling two T1-species can be achieved by a timed combination of two non-selective inversion pulses. However, due to their similar T1 values, the contrast between infarct and blood is still small.

Additionally, techniques are known that decouple blood preparation from tissue preparation by use of a non-selective inversion followed by a slice-selective "re-inversion" followed by image acquisition ("Black Blood HASTE"). Such techniques work well because there is sufficient time for blood exchange and preparation and readout occur when the heart is in nearly the same position (before contraction and during mid to late diastole, respectively). However, a recurring problem has been that the standard classic double-inversion "dark blood" approach does not work in conjunction with delayed enhancement since the contrast agent is present and since only one T1 species is nulled and so cannot be used for viability imaging without adding further preparation pulses. There are therefore challenges associated with using the classic approaches for dark blood viability. For example, the classic dark blood preparation does not provide T1-weighting of the tissue. An additional IR pulse would need to be played before or after to double-IR dark blood preparation to get dark blood delayed enhancement images. Generally, the simultaneous nulling of blood and normal myocardium would be extremely difficult as there may be insufficient blood exchange between double IR preparation and image readout.

Dark blood delayed enhancement techniques that could image blood and normal myocardium as dark/black while leaving the infarct bright would be clinically useful. For example, it would be desirable to provide techniques which would:

Null blood and normal myocardium at the time of readout;
Play slice-selective preparation before systolic contraction (blood exchange, slice position);
Provide image readout late enough (blood exchange, similar slice position as during slice-selective preparation); and
Allow a non-selective preparation to be played out at any time.

The idea of nulling more than one type of tissue per se is known. However, to our knowledge, it has not generally been used in a combination of early slice-selective preparation, blood exchange of the heart, and late non-selective preparation in the presence of MR-contrast agent to acquire "black-blood viability" images (note that in this context, "viability" refers to the property of heart tissue, myocardium, of being alive, "viable", or dead, "non-viable").

We have now developed a new "dark blood" or "black blood" myocardial viability delayed enhancement imaging technique which can obtain dark blood delayed enhancement images by a timed combination of a selective preparation after the cardial R-wave and a later, non-selective inversion. Such MRI sequences can aid the detection of small subendocardial infarcts.

One exemplary illustrative non-limiting implementation combines an early slice-selective magnetic preparation of heart tissue, followed by a particular calculated delay to allow blood exchange of the heart, followed by late non-selective inversion (e.g., in the following heartbeat). The timed combination of slice-selective and non-selective preparation decouples the infarct-curve from the blood-curve and enables greater image contrast than is possible for example using two non-selective preparations.

In one exemplary illustrative non-limiting implementation, to make both blood and non-infarcted myocardium appear black in the image, a preparation is used to cause the relaxation curves of both T1-species to simultaneously cross the zero-line ("be nulled"). In one exemplary illustrative non-limiting implementation, the timed combination of slice-selective and non-selective preparation decouples the infarct from the blood curve and enables good image contrast.

In one exemplary illustrative non-limiting implementation, the time from the nsIR (non-selective inversion recovery) to the center of K-space is chosen to null blood and only depends on its T1. The time between the SSSR (slice-selective saturation recovery) pulse and nsIR pulse is set to null normal myocardium when blood is nulled.

In one exemplary illustrative non-limiting implementation, contrast between infarct and blood is improved at the expense of a lower infarct signal-to-noise ratio. Gradient, turbo-spin echo (tse) and SSFP readouts can be used. The tse readout results in a high signal to noise ratio and better blood nulling.

BRIEF DESCRIPTION OF THE DRAWINGS

These and other features and advantages will be better and more completely understood by referring to the following detailed description of exemplary non-limiting illustrative embodiments in conjunction with the drawings of which:

FIG. 2C shows exemplary illustrative non-limiting partial inversion black blood viability sequences;
FIG. 2D shows example slice-selective preparation and blood-exchange and data readout during mid to late diastole;
FIG. 2E shows an exemplary illustrative non-limiting user interface screen;
FIG. 3 shows an exemplary illustrative non-limiting preparation including slice-selective saturation and non-selective inversion;
FIG. 3A shows an exemplary illustrative non-limiting slice-selective saturation and non-selective inversion pulse sequence;
FIG. 3B shows exemplary illustrative non-limiting magnetizations corresponding to FIGS. 3 & 3A;
FIGS. 3C-1 & 3C-2 show exemplary illustrative non-limiting comparison images;
FIG. 4 shows an exemplary illustrative non-limiting preparation including slice-selective inversion and non-selective inversion;
FIG. 4A shows an exemplary illustrative non-limiting slice-selective inversion and non-selective inversion pulse sequence;
FIG. 4B shows exemplary illustrative non-limiting magnetizations corresponding to FIGS. 4 & 4A;
FIGS. 4C-1 and 4C-2 show exemplary illustrative non-limiting comparison images;
FIGS. 5A, 5B and 5C show images developed using standard "bright blood", IRIR Gradient Echo (GRE) "black blood" and IRIR Turbo Spin Echo (TSE) "black blood" readouts, respectively;

FIG. 6 shows a further exemplary illustrative non-limiting preparation including a partial selective inversion followed by a non-selective inversion;

FIG. 7 presents another exemplary illustrative non-limiting preparation including two selective inversions and a non-selective inversion;

FIG. 8 shows an exemplary illustrative pulse sequence corresponding to FIG. 7;

FIG. 9 shows an exemplary illustrative non-limiting preparation including a non-selective inversion followed by a timed classic double inversion;

FIG. 10 shows an exemplary illustrative non-limiting preparation including a slice-selective inversion followed by a timed classic double inversion;

FIGS. 11A, 12A, 13A and 14A show example infarcted dog heart imaging results without black blood preparation techniques;

FIGS. 11B, 12B, 13B and 14B show example infarcted dog heart imaging results using black blood preparation techniques;

DETAILED DESCRIPTION OF EXEMPLARY ILLUSTRATIVE NON-LIMITING IMPLEMENTATIONS

Figure 1:
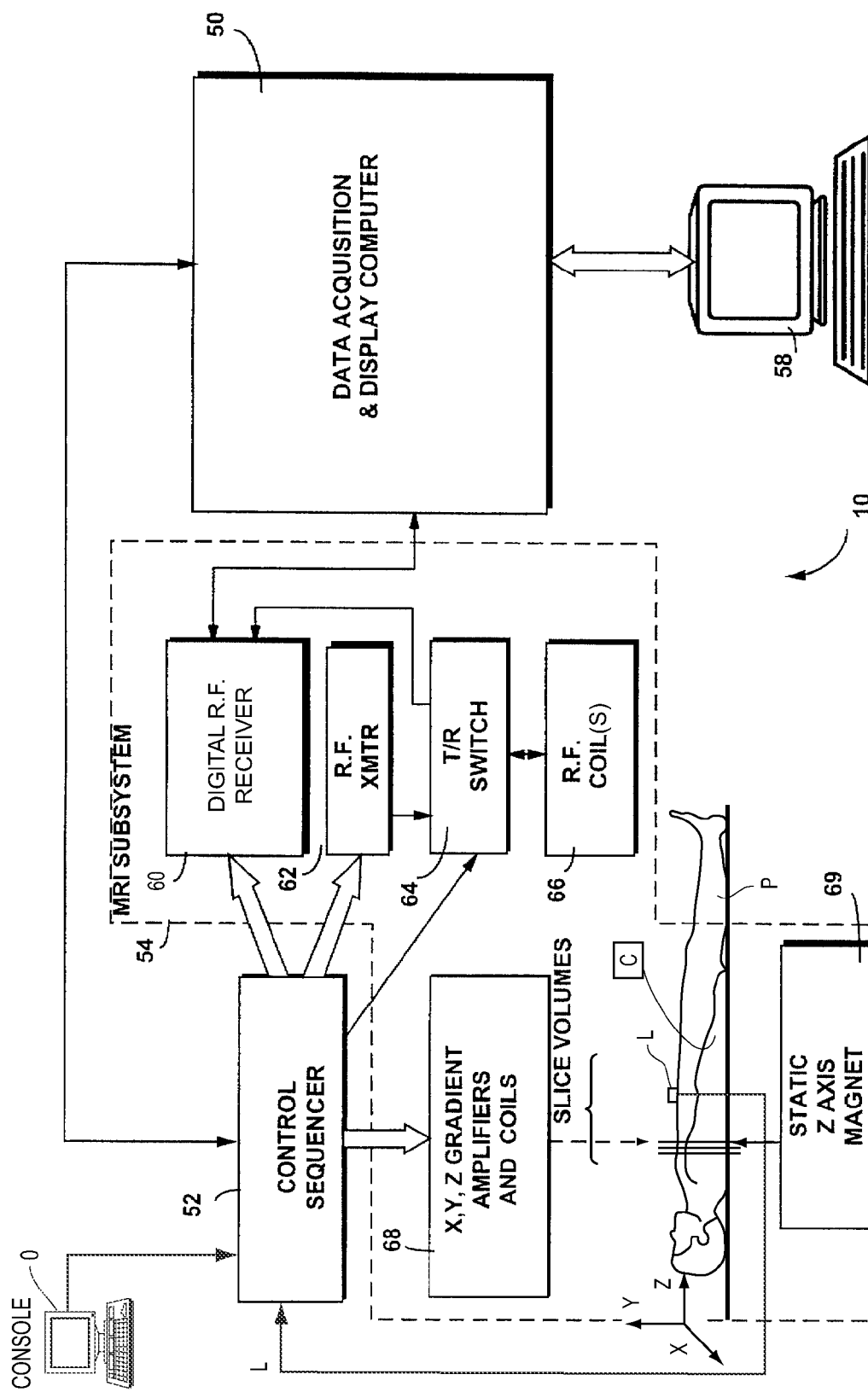
FIG. 1 shows an example a cardial MRI system.

The exemplary illustrative non-limiting technology herein can be implemented on any commercial cardiac MRI scanner. No additional hardware is required. FIG. 1 shows an example such magnetic resonance imaging ("MRI") system 10 including a data acquisition and display computer 50 coupled to an operator console O, a MRI real-time control sequencer 52, and a MRI subsystem 54. MRI subsystem 54 includes XYZ magnetic gradient coils and associated amplifiers 68, a static Z-axis magnet 69, a digital RF transmitter 62, a digital RF receiver 60, a transmit/receive switch 64, and RF coil(s) 66. As is well known, a dedicated cardiac or torso phased-array coil is typically used for cardiac imaging. Electrocardiogram (ECG) leads L are used in cardiac imaging to synchronize control sequencer 52 with electrical stimulation of the heart by the brain.

One exemplary illustrative non-limiting implementation uses a clinical MR scanner (Magnetom Sonata, Siemens Medical Solutions) set with parameters including field of view 300 mm, matrix 256×114, TE 3.85 ms, spatial resolution 1.6×1.6×6 mm, lines per segment 19, bandwidth 160 Hz/pixel, acquisition duration 18 heartbeats. The timings specified herein are applicable to MRI scanners with 1.5 Tesla field strength, but this is by way of example only. At higher Tesla field strengths, the relaxation time T1 increases and the time delays should be increased accordingly.

Subsystem 54 is controlled in real time by sequencer 52 to generate magnetic and radio frequency fields that stimulate nuclear magnetic resonance ("NMR") phenomena in an object P (e.g., a human body) to be imaged. A suitable well known contrast agent (C) such as for example Kg Gd-DTPA is injected intravenously into the patient P in a well known manner. A resulting image of patient P on display 58 shows cardiac features and structures that cannot be seen using X-ray, ultrasound or other medical imaging techniques. In the exemplary illustrative non-limiting implementation, the resulting dark or black blood myocardial viability imaging shows blood and healthy myocardium as black or dark and shows infarcts (including subendocardial infarcts) as bright.

Exemplary Techniques For Nulling Both Blood And Normal Myocardium

In one exemplary illustrative non-limiting implementation, we program the control sequencer 52 of such conventional MRI equipment to generate a pulse sequence that combines an early slice-selective magnetic preparation of heart tissue followed by a later global (hereafter referred to as "non-selective") preparation. Unlike the traditional "black-blood" approaches, the preparations are not played back to back but rather are planned with a calculated delay between them. The timed combination of both preparations allows a subsequent readout process to render both normal myocardium and blood dark, and infarcted territory bright.

Figure 2A:
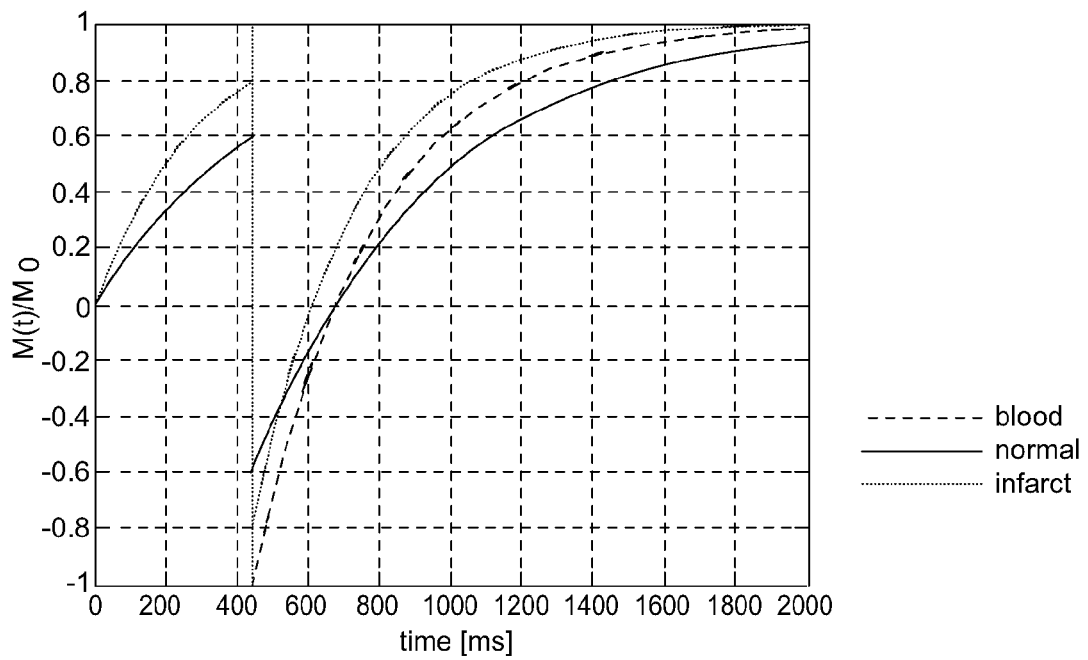
FIGS. 2A and 2B show example relaxation curves.

FIG. 2A shows relaxation curves for normal myocardium, -infarct, and blood about 15 minutes after IV injection of 0.125 mmol/Kg Gd-DTPA contrast agent (T1 blood=330 ms, T1 normal=490 ms, T1 infarct=280 ms). As is well known, a contrast agent such as Gadolinium will tend to concentrate in the infarcted myocardial tissue but not in healthy or normal myocardium—allowing infarct myocardium and normal myocardium to be distinguished and the normal myocardium to be nulled. However, as can be seen in FIG. 2A, blood tends to exhibit nearly the same relaxation time as infarct myocardium due to the contrast agent being present in the blood pool and thus generates nearly the same signal—sometimes resulting in poor infarct/blood contrast.

Figure 2B:
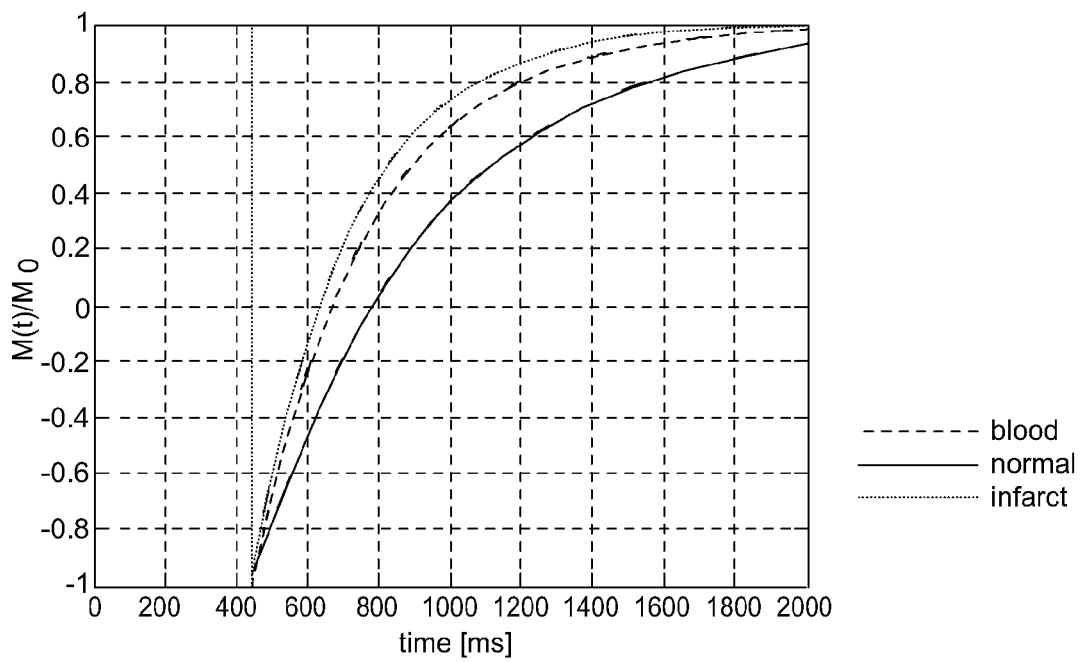

Timing and relaxation curves for an exemplary illustrative non-limiting double-preparation pulse sequence consisting of a slice-selective preparation (in this case a slice-selective saturation (SSSR)) followed by a non-selective inversion (NSIR) are shown in FIG. 2B. The timed combination of slice-selective and non-selective preparation decouples the infarct relaxation curve from the blood-curve and enables greater image contrast than is possible with two non-selective preparations. The time from the NSIR to the center of k-space is chosen to null blood and depends only on its T1. The time between the SSSR and NSIR pulse is set to null normal myocardium at the same time blood is nulled.

Exemplary Illustrative Non-Limiting NMR Pulse Sequences

FIG. 2C shows an exemplary illustrative non-limiting black blood viability MRI sequence based on the FIG. 2B approach but the slice selective pulse is a partial inversion pulse and not a saturation pulse which does not affect the concept but lengthens the timing between slice selective and non-selective preparation. FIG. 2D shows an exemplary illustrative non-limiting series of diagrams illustrating corresponding slice-selective preparation and blood exchange within the heart.

As shown in FIG. 2C, prior to systole (i.e., after R-wave or during previous heartbeat), sequencer 52 controls the MRI subsystem 54 to generate a first preparation slice-selective partial inversion RF pulse within a particular slice of the heart. The slice-selective preparation is done at any time during one heartbeat or soon after the R-wave of the following, before cardiac contraction starts (see panel A of FIG. 2D).

This first, slice-selective preparation causes the magnetization orientation of the spin axes within the myocardium within the slice to at least partially invert. As soon as the RF pulse ends, the protons within the myocardium begin to relax. As is well known, the contrast agent modifies the proton relaxation times of the infarct myocardium in which it is concentrated. Therefore, the normal and infarct myocardium relax at different rates (in this example, the infarct protons relax and return to steady state more rapidly due to the presence of the contrast agent).

The sequencer 52 then controls—at an appropriate timing—the MRI subsystem 54 to generate a further preparation RF pulse in the form of a non-selective inversion RF pulse during the following heartbeat. At this point in time, the heart has entered its systolic phase and the ventricles have contracted to drive blood through the aorta and pulmonary artery (see FIG. 2D, panel B). Blood that has seen the early slice-selective preparation is thus expelled from the slice (panel B). Therefore, the blood previously prepared by the first slice-selective partial inversion RF pulse is mostly no longer within the heart (having been expelled during systole).

This second, global inversion preparation, being non-selective, is applied to all tissue in the heart as well as to all blood in and near the heart. This non-selective inversion RF pulse causes the magnetization (orientation) of the proton spin axes within all relevant structures (normal myocardium, infarct myocardium and blood) to invert. However, due to the previous slice-selective preparation which prepared the myocardium but not the blood, the relaxation of each of the three structure categories (blood, normal myocardium, and contrast-concentrated infarct myocardium) begins at different magnetizations as shown in FIG. 2C. Furthermore, since the blood protons and the normal myocardium protons have different relaxation rates, their relaxation curves intersect at a point X at a particular point in time t—and the relaxation curve of the infarct protons (which are relaxing at a still different rate) does not intersect at this same point X.

In the exemplary illustrative non-limiting implementation, data readout takes place during the diastolic phase (FIG. 2D panel C) when new blood has begun to fill the heart. The protons within this new blood have not been prepared by the previous slice-selective preparation pulse because they were not within the slice previously prepared by the slice-selective partial inversion. During data readout, only blood that has experienced the late non-selective preparation (but not the early slice-selective preparation) is present in the slice. Preparation of heart tissue and blood are thus decoupled. In the exemplary illustrative non-limiting implementation, the non-selective pulse can come before all selectively excited blood has been expelled so long as substantially all selectively excited blood has been expelled at the time of readout.

By timing readout appropriately based on the intersection of the relaxation curves, we have the opportunity to null both the unprepared blood protons and the normal myocardium protons (to provide dark or black portions of the image) while enhancing the portions of the image corresponding to myocardium infarct (so that those image portions appear bright).

FIG. 2E shows an exemplary illustrative non-limiting implementation of a user interface that may be displayed on the operator console to provide the FIG. 2C pulse sequence. This exemplary screen shows input boxes for the inversion times T1 for normal (living) myocardium and blood. It also shows thickness of the preparation slice in % which usually does not need to be adjusted. Using these simple parameters in a clinical setting, the MRI operator can control the quality of the imaging results using the exemplary illustrative non-limiting implementation. In general, adjusting the timing between all preparation pulses and the readout module can be time-consuming. To simplify the operation of the sequences for the user, in one exemplary illustrative non-limiting implementation, the timing is automatically calculated by the user interface of the sequence. The user still needs to know the relaxation times of "normal myocardium" and blood, but the timing is then calculated based on these provided numbers. Different formulas are used for each method.

EXAMPLE PREPARATION

Selective Saturation Followed By Non-Selective Inversion

FIG. 3 shows the magnetization recovery of normal myocardium, infarct, and blood as occurring in an exemplary illustrative non-limiting implementation providing a slice-selective saturation pulse (SS SR) followed by a non-selective inversion. The curves shown are for typical relaxation constants (T1-valued) 10-20 minutes after an administration of a 1.25 mmol/Kg dose of contrast agent. The T1-values used in this and the following simulations are T1 infarct=280 ms, T1 normal=490 ms, and T1 blood=330 ms. These values change as a function of time after contrast agent injection, and modify the timing of the pulses needed to make blood and normal myocardium black.

In this particular non-limiting illustrative implementation, the slice-selective saturation recovery pulse (SS SR) sets the magnetization of infarct and "normal" to zero. The magnetization of both tissue types recover and is experiencing a non-selective inversion recovery pulse (NS IR) 440 ms later. The inverted magnetizations continue to recover, now from different starting points. The magnetization of "new" blood (i.e., blood that was not within the heart during the first preparation) that was unaffected by the SS SR pulse is now inverted and recovers as well, starting from −M0. Due to the time between both preparations, the blood and the "normal" curve cross zero at the same time. If data is acquired at that time, they do not yield any signal (they have no magnetization) and thus appear black. "Infarct" has positive magnetization giving rise to a bright signal in the resulting image.

FIG. 3A shows an example pulse sequence to accomplish the method described above in connection with FIG. 3. Note the two preparation pulses (a slice-selective saturation pulse followed by a non-selective inversion pulse). Conventional readout pulses follow.

FIG. 3B shows how slice-selective saturation and non-selective preparation affect magnetization. The first panel (all the way to the left) shows magnetization vectors for infarct, blood and normal myocardium all at +M0. An infarct region is marked by a dotted white line and two "normal" regions are delineated by a dotted black line.

The slice-selective saturation preparation shown in the FIG. 3B second panel erases the magnetization in the slice. The magnetization in the slice then recovers to different values depending on the tissue type (see center panel 3). After the following non-selective inversion preparation in panel 4, blood magnetization is at −M0, and "normal" and infarct are between −M0 and zero. "Normal" is closer to zero, but will recover slower than infarct.

At the time of data readout (right hand panel 5), magnetization of blood and normal myocardium have both recovered to zero, but they did so from different starting points and with different speed. Infarct has faster recovery and has positive magnetization at that time.

FIG. 3C-2 shows an example image obtained from the above-described preparation using selective saturation followed by non-selective inversion. As compared to FIG. 3C-1 (current standard of clinical practice NSIR), one can see that the FIG. 3C-2 image allows the bright infarct to be more clearly seen because it is not obscured by bright surrounding blood.

EXAMPLE

Selective Inversion Followed By Non-Selective Inversion

FIG. 4 shows an exemplary illustrative non-limiting implementation wherein the first preparation is a slice-selective inversion (SSIR) rather than a slice-selective saturation. Using a slice-selective inversion pulse allows a longer time between slice-selective preparation and data readout. More blood exchange can take place—making the method more robust to slow blood flow (which often occurs in patients with infarcts) and more user-friendly. A potential disadvantage is a lower signal from the infarct, leading to noisier images (more speckles).

FIG. 4A shows a corresponding exemplary pulse sequence. Note the first, slice-selective inversion preparation RF pulse followed by a non-selective inversion RF pulse.

FIG. 4B shows how slice-selective inversion and non-selective preparation affect magnetization during the FIG. 4B sequence. The first (left-most) panel shows magnetization vectors all at +M0. As described above in connection with FIG. 3B, an infarct region is marked by a dotted line, two "normal" regions by a dotted black line.

The slice-selective inversion preparation shown in panel 2 inverts the magnetization in the slice. The magnetization in the slice then recovers to different values depending on the tissue type (panel 3). After the second preparation pulse (non-selective inversion) in panel 4, blood magnetization is at −M0, and "normal" and infarct are between −M0 and zero. "Normal" is closer to zero, but will recover slower than infarct. At the time of data readout magnetization of blood normal myocardium have both recovered to zero, but they did so from different starting points and with different speed. Infarct has faster recovery and has positive magnetization at that time.

FIG. 4C-2 shows an example image obtained from the above-described preparation using selective saturation followed by non-selective inversion. As compared to FIG. 4C-1 (current standard of clinical practice NSIR), one can see that the FIG. 4C-2 image allows the bright infarct to be more clearly seen because it is not obscured by bright surrounding blood.

Exemplary Readout Techniques

The exemplary pulse sequences described above make use of conventional readout sequences. Two common readout sequences are the so-called "gradient echo" (GRE) readout and the "Turbo Spin Echo (TSE). Any other pulse sequence readout technique may be used such as steady state free precession (SSFP) also known under the vendor acronyms True Fisp (Siemens) and FIESTA (GE). FIGS. 5A, 5B and 5C show a comparison of the standard (bright-blood) technique on the left, the black blood with GRE in the center, and the black blood with TSE readout on the right. The higher signal of the latter (less speckles) can be seen.

EXAMPLE

Partial Selective Inversion Followed By Non-Selective Inversion

FIG. 6 shows a further exemplary illustrative non-limiting implementation using a preparation consisting of a partial selective inversion followed by a non-selective inversion. A partial selective inversion or saturation (by way of example, a 50% inversion is shown in FIG. 6) allows modifying the time delay between first and second preparation event by varying the degree of inversion or saturation. The shortest delay is obtained with a partial saturation, the longest with an inversion pulse. An advantage of this implementation is that by varying the degree of saturation or inversion, the timing can be adjusted so that the slice selective preparation always occurs right after the R-wave, and the readout in mid to late diastole, irrespective of the heartbeat duration. These are the best locations for preparation and data readout which may not be obtained due to timing requirements conflicting with the length of a heartbeat.

EXAMPLE

Two Selective Inversions Followed By Non-Selective Inversion

FIG. 7 presents another variation on the idea of making both blood and "normal" dark at the same time. In this exemplary illustrative non-limiting implementation, two SS IR pulses are followed by a NS IR pulse. FIG. 8 shows a corresponding exemplary pulse sequence. An advantage of this method is improved signal of the infarct. A disadvantage is the need to adjust two time delays instead of one, which reduces its ease of use. This could be overcome with timing calculations implemented in the user interface.

EXAMPLE

Non-Selective IR Followed By Timed Classic Double IR

FIGS. 9 and 10 show additional exemplary illustrative non-limiting implementations providing triple inversion recovery "triple IR" type preparation schemes. The T1-values used in the recovery curves simulations in FIGS. 9 and 10 are T1 infarct=280 ms, T1 normal=490 ms, and T1 blood=330 ms in this particular example.

In the exemplary illustrative non-implementations shown in FIGS. 9 and 10, a preparation pulse is played at the beginning of the preparation scheme and is later followed by a so-called double-IR preparation. The time between the first preparation and the double-IR preparation is of the essence. The combination of a preparation, an exact time delay, and this classic DIR provides useful results.

The double-IR preparation is widely used in MRI. We will refer to it as "classic double IR or classic DIR". This classic DIR preparation consists of a non-selective inversion immediately followed by a slice-selective inversion. Therefore, the slice seeing this preparation is untouched (inverted, then immediately re-inverted) whereas the blood and tissue outside the slice is inverted. Later, at the time of data readout, the outside (inverted) blood has entered the slice and is differently prepared than the slice itself. For our dark blood purposes, playing out the classic DIR in reverse order (slice-selective inversion immediately followed by a non-selective inversion) will work better. This is not the classic DIR preparation but most likely patent protected already.

In more detail, FIG. 9 shows a non-selective IR followed by a timed wait—then a classic DIR—followed by another timed wait—followed by a readout. The non-selective IR inverts the signal of blood, normal myocardium, and infarct. After this event, the blood, normal myocardium, and infarct signal recovers. A later classic DIR leaves the normal myocardium and infarct untouched, but selectively inverts the blood. If the correct wait time is chosen, the blood curve and the normal myocardium curve will cross zero ("be nulled, have dark image intensity") at the same time, whereas infarct already has recovered more and has a positive signal (bright image intensity). That is the time-point when the data is read out FIG. 10 shows an exemplary illustrative implementation providing a slice-selective IR—followed by a timed wait—followed by a classic DIR—followed by another wait—followed by a readout. The slice-selective IR inverts the signal of normal myocardium and infarct, but leaves the blood untouched. After this event, the normal myocardium, and infarct signal recovers, blood is still at +M0. A later classic DIR leaves the normal myocardium and infarct untouched, but selectively inverts the blood. If the correct wait time is chosen, the blood curve and the normal myocardium curve will cross zero ("be nulled, have dark image intensity") at the same time, whereas infarct already has recovered more and has a positive signal (bright image intensity). The time from classic DIR to data readout is longer than in idea A making it more robust.

Note that in both FIG. 9 and FIG. 10, the first preparation pulse is played in the diastole of the previous heartbeat. This ensures that the classic DIR preparation is played early enough so that fresh blood can enter the imaged slice before the data readout. Otherwise blood would not appear black in the image (There would still be blood hanging around in the imaged slice that saw the slice-selective preparations).

A potential disadvantage of the FIGS. 9 and 10 pulse sequences is that they may be less robust than the previous ones due to a smaller "wait again" time (see figures) between the selective prep part of the classic DIR* and the data readout. However, we expect the FIG. 10 pulse sequence to be robust enough, and possibly more robust than the FIG. 9 pulse sequence.

Example Imaging Results

FIGS. 11A and 11B show exemplary imaging results with a dog heart. FIG. 11A uses a standard bright blood technique currently used in clinical practice. FIG. 11B is an example image of the new black blood approach.

FIGS. 12A and 12B show exemplary imaging results with another dog heart. FIG. 12A uses a standard bright blood technique currently used in clinical practice. FIG. 12B is an example image of the new black blood approach.

Figure 13B:
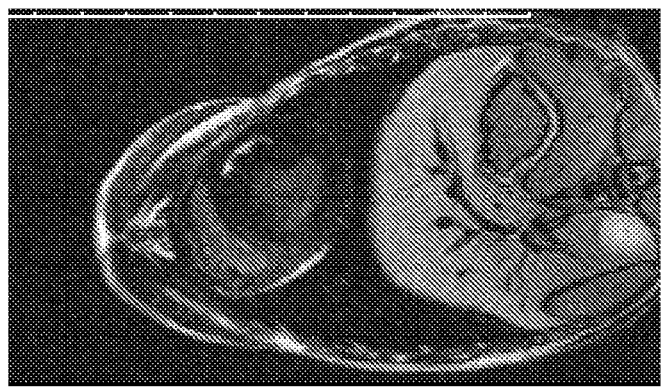
Figure 13A:
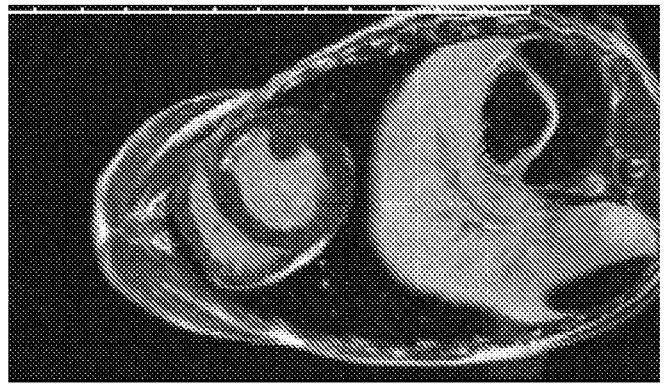

FIGS. 13A and 13B show exemplary imaging results with another dog heart. FIG. 13A uses a standard bright blood technique currently used in clinical practice. FIG. 13B is an example image of the new black blood approach.

Figure 14B:
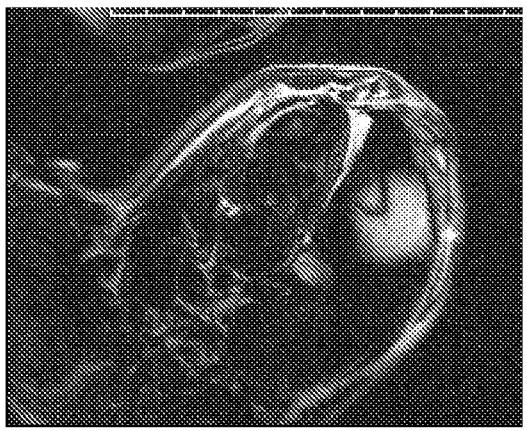
Figure 14A:
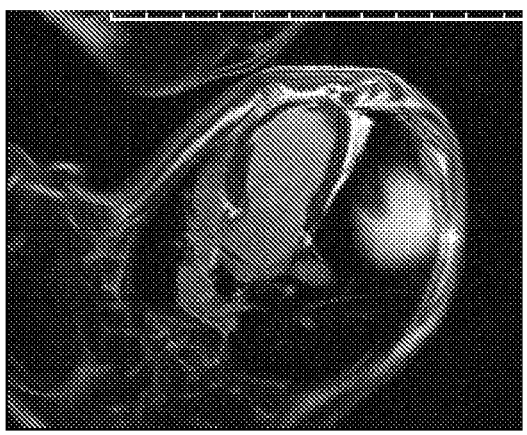

FIGS. 14A and 14B show exemplary imaging results with another dog heart. FIG. 14A uses a standard bright blood technique currently used in clinical practice. FIG. 14B is an example image of the new black blood approach.

Figure 15C:
FIGS. 15C and 16C show infarcted human heart imaging results developed using black blood preparation and Turbo spin echo readout.
Figure 15B:
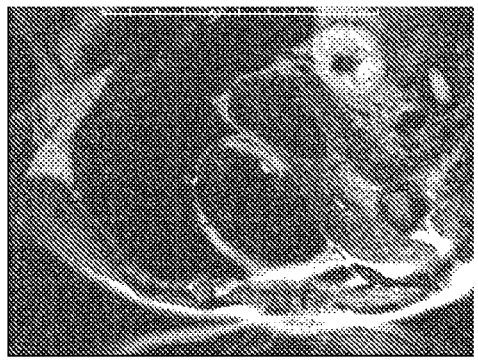
FIGS. 15B and 16B show infarcted human heart imaging results developed using black blood preparation and gradient echo readout.
Figure 15A:
FIGS. 15A and 16A show infarcted human heart imaging results images developed using standard techniques.

FIGS. 15A, 15B and 15C show exemplary imaging results for an infarcted human heart. FIG. 15A shows a conventional clinical bright blood approach. FIGS. 15B and 15C show exemplary images resulting from the new black blood approach.

Figure 16C:
Figure 16B:
Figure 16A:

FIGS. 16A, 16B and 16C show exemplary imaging results for an infarcted human heart. FIG. 16A shows a conventional clinical bright blood approach. FIGS. 16B and 16C show exemplary images resulting from the new black blood approach.

The exemplary illustrative non-limiting technology herein has the capability of being extremely useful. Such a method has been sought after by the cardiac MR community for many years. The visualization of subendocardial infarcts would be possible or tremendously facilitated by this technique. Lives may be saved or extended as a result.

All documents cited herein are hereby incorporated by reference as if expressly set forth.

While the technology herein has been described in connection with exemplary illustrative non-limiting embodiments, the invention is not to be limited by the disclosure. The invention is intended to be defined by the claims and to cover all corresponding and equivalent arrangements whether or not specifically disclosed herein.

We claim:

1. A magnetic resonance imaging method comprising:
   injecting a live patient with a paramagnetic contrast agent that collects within dead heart tissue;
   applying a nuclear magnetic resonance (NMR) slice-selective preparation pulse to the patient's chest;
   waiting a first delay time that is a function of both: (a) healthy heart tissue longitudinal relaxation time T1 and (b) a second delay time such that the patient's blood appears nulled based on the blood longitudinal relaxation time T1;
   then applying a nuclear magnetic resonance non-spatially selective inversion preparation pulse to the patient's chest;
   then waiting the second delay time to allow blood the patient's heart contained at the time of said slice-selective preparation pulse to be expelled from the patient's heart;
   then acquiring NMR echoes conditioned by the preparation pulses and first and second delay times so that magnetization of healthy heart tissue and blood are substantially the same; and
   generating an image based on said acquired NMR echoes, wherein the image shows normal heart tissue and blood within the patient's heart as the same color or intensity and shows the patient's dead heart tissue as a different color or intensity.

2. The method of claim 1 further including using a specific combination of said first delay time and second delay time to force the magnetization of normal heart tissue and the blood within the patient's heart to be substantially the same and to be substantially zero.

3. A cardiac imaging method comprising:
   applying a preparation to a beating heart containing blood, the preparation comprising a slice-selective preparation pulse followed by a non-spatially selective inversion preparation pulse with a timed wait therebetween, said timed wait being a function of both (a) healthy heart tissue longitudinal relaxation time T1 and (b) a further delay such that blood which will be within the beating heart at the time of read out is nulled based on blood longitudinal relaxation time T1;
   after waiting the second delay time to allow the patient's heart to expel blood the heart contained at the time of said slice-selective preparation pulse, reading out nuclear magnetic resonance echoes from the beating heart at a time when relaxation of blood and non-infarcted myocardium are nulled together; and
   generating an image from said echoes showing non-infarcted myocardium and blood as dark and infarcted myocardium as bright.

4. A cardiac imaging method comprising:
   applying at least one slice-selective preparation pulse to a heart containing blood;
   applying a slice-selective preparation pulse, then waiting a delay that is a function of both (a) healthy heart tissue longitudinal relaxation time T1 and (b) a second delay time such that the blood is nulled based on the blood longitudinal relaxation time T1, and then applying a non-spatially selective preparation pulse to the heart;

then waiting until blood within the heart at the time of the slice-selective preparation pulse has been expelled from the heart;

then reading out nuclear magnetic resonance (NMR) echoes from the heart at a time when relaxation of blood and non-infarcted myocardium are nulled together so that magnetization of healthy heart tissue and blood are substantially the same; and generating an image, based on said read-out NMR echoes, showing non-infarcted myocardium and blood as dark and infarcted myocardium as bright.

5. The method of claim 4 wherein said slice-selective preparation pulse comprises a selective partial inversion pulse.

6. The method of claim 4 wherein said slice-selective preparation pulse comprises a saturation pulse.

7. The method of claim 4 wherein said slice-selective preparation pulse comprises an inversion pulse.

8. The method of claim 4 wherein said slice-selective preparation pulse comprises plural selective inversion pulses.

9. The method of claim 4 wherein said reading out comprises gradient echo readout.

10. The method of claim 4 wherein said reading out comprises turbo spin echo readout.

11. The method of claim 4 wherein said reading out comprises steady-state free precession (SSFP) readout.

12. A cardiac imaging method comprising:
applying at least one inversion pulse to a patient's chest;
waiting a delay time that is a function of both (a) healthy heart tissue longitudinal relaxation time T1, and (b) blood longitudinal relaxation time T1;
then applying a second, non-spatially selective double inversion pulse to the patient's chest;
then waiting until at least some of the blood present in the patient's heart during the at least one inversion pulse has been expelled from the patient's heart;
then reading out nuclear magnetic resonance (NMR) echoes from the heart at a time when relaxation of blood and non-infarcted myocardium are nulled together; and
generating an image, based on said read-out NMR echoes, showing non-infarcted myocardium and blood as dark and infarcted myocardium as bright.

13. The method of claim 12 wherein said at least one inversion pulse is slice-selective.

14. The method of claim 12 wherein said at least one inversion pulse is non-slice-selective.

15. The method of claim 12 wherein the reading out comprises one of spin echo readout, gradient echo readout and steady-state free precession (SSFP) readout.

* * * * *